(12) United States Patent
Greenfeder et al.

(10) Patent No.: US 7,422,742 B2
(45) Date of Patent: Sep. 9, 2008

(54) METHODS FOR USING HUMAN MONOCLONAL ANTIBODIES TO INTERLEUKIN-5

(75) Inventors: Scott Greenfeder, Metuchen, NJ (US); Jose Corvalan, Foster City, CA (US)

(73) Assignees: Schering Corporation, Kenilworth, NJ (US); Abgenix, Inc., Fremont, CA (US)

( * ) Notice: Subject to any disclaimer, the term of this patent is extended or adjusted under 35 U.S.C. 154(b) by 0 days.

(21) Appl. No.: 11/542,943

(22) Filed: Oct. 4, 2006

(65) Prior Publication Data

US 2007/0025994 A1 Feb. 1, 2007

Related U.S. Application Data

(62) Division of application No. 10/401,344, filed on Mar. 27, 2003, now Pat. No. 7,141,653.

(60) Provisional application No. 60/369,044, filed on Mar. 29, 2002, now abandoned.

(51) Int. Cl.
A61K 39/395 (2006.01)
(52) U.S. Cl. .................................. 424/141.1; 424/145.1
(58) Field of Classification Search ........................ None
See application file for complete search history.

(56) References Cited

U.S. PATENT DOCUMENTS

| | | | |
|---|---|---|---|
| 5,096,704 A | 3/1992 | Coffman et al. |
| 5,545,806 A | 8/1996 | Lonberg et al. |
| 5,545,807 A | 8/1996 | Surani et al. |
| 5,591,669 A | 1/1997 | Krimpenfort et al. |
| 5,612,205 A | 3/1997 | Kay et al. |
| 5,625,126 A | 4/1997 | Lonberg et al. |
| 5,633,425 A | 5/1997 | Lonberg et al. |
| 5,643,763 A | 7/1997 | Dunn et al. |
| 5,661,016 A | 8/1997 | Lonberg et al. |
| 5,683,892 A | 11/1997 | Ames, Jr. et al. |
| 5,721,367 A | 2/1998 | Kay et al. |
| 5,770,429 A | 6/1998 | Lonberg et al. |
| 5,789,215 A | 8/1998 | Berns et al. |
| 5,789,650 A | 8/1998 | Lonberg et al. |
| 5,814,318 A | 9/1998 | Lonberg et al. |
| 5,877,293 A | 3/1999 | Adair et al. |
| 5,886,152 A | 3/1999 | Nakatani et al. |
| 5,916,771 A | 6/1999 | Hori et al. |
| 5,939,598 A | 8/1999 | Kucherlapati et al. |
| 5,985,615 A | 11/1999 | Jakobovits et al. |
| 5,994,619 A | 11/1999 | Stice et al. |
| 5,998,209 A | 12/1999 | Jakobovits et al. |
| 6,054,297 A | 4/2000 | Carter et al. |
| 6,075,181 A | 6/2000 | Kucherlapati et al. |
| 6,091,001 A | 7/2000 | Jakobovits et al. |
| 6,114,598 A | 9/2000 | Kucherlapati et al. |
| 6,129,913 A | 10/2000 | Ames et al. |
| 6,130,364 A | 10/2000 | Jakobovits et al. |
| 6,632,927 B2 | 10/2003 | Adair et al. |
| 7,141,653 B2 | 11/2006 | Greenfeder et al. |
| 2002/0142374 A1 | 10/2002 | Gallo et al. |

FOREIGN PATENT DOCUMENTS

| | | |
|---|---|---|
| EP | 0267779 | 5/1988 |
| EP | 0367596 A1 | 5/1990 |
| WO | WO 91/10741 | 7/1991 |
| WO | WO 92/01047 | 1/1992 |
| WO | WO 93/06213 | 4/1993 |
| WO | WO 93/16184 | 8/1993 |
| WO | WO 94/02602 | 2/1994 |
| WO | WO 96/33735 | 10/1996 |
| WO | WO 96/34096 | 10/1996 |
| WO | WO 98/16654 | 4/1998 |
| WO | WO 98/24893 | 6/1998 |
| WO | WO 98/50433 | 11/1998 |
| WO | WO 99/45031 | 9/1999 |
| WO | WO 99/53049 | 10/1999 |
| WO | WO 00/09560 | 2/2000 |
| WO | WO 00/37504 | 6/2000 |
| WO | WO 01/62287 A1 | 8/2001 |

OTHER PUBLICATIONS

Wilson et al. (2005) Journal of Experimental Medicine, vol. 202, No. 9, 2005, pp. 1199-1212.*

Maynard, Jennifer, et al., "Antibody Engineering", *Annu. Rev. Biomed. Eng.*, vol. 02:339-76 (2000).

Green, Larry L., "Antibody engineering via genetic engineering of the mouse: XenoMouse strains are a vehicle for the facile generation of therapeutic human monoclonal antibodies", *Journal of Immunological Methods*, vol. 231:11-23, (Dec. 1999).

(Continued)

*Primary Examiner*—Prema Mertz
(74) *Attorney, Agent, or Firm*—Gloria M. Fuentes

(57) ABSTRACT

The present invention relates to antibodies and antigen-binding portions thereof that specifically bind to interleukin 5 (IL-5), which is preferably human IL-5. The invention also relates to human anti-IL-5 antibodies, including chimeric, bispecific, derivatized, single chain antibodies or portions of fusion proteins. The invention also relates to isolated heavy and light chain immunoglobulin molecules derived from anti-IL-5 antibodies and nucleic acid molecules encoding such molecules. The present invention also relates to methods of making anti-IL-5 antibodies, pharmaceutical compositions comprising these antibodies and methods of using the antibodies and compositions thereof for diagnosis and treatment. The invention also provides gene therapy methods using nucleic acid molecules encoding the heavy and/or light immunoglobulin molecules that comprise the human anti-IL-5 antibodies. The invention also relates to gene therapy methods and transgenic animals comprising nucleic acid molecules of the present invention.

6 Claims, No Drawings

OTHER PUBLICATIONS

Dickason, Richard R., et al., "Delineation of IL-5 Domains Predicted to Engage the IL-5 Receptor Complex", *The Journal of Immunology*, vol. 156:1030-1037, (Feb. 1996).

Cornelis, Sigrid, et al., "Detailed analysis of the IL-5-IL5Ralpha interaction: characterization of crucial residues on the ligand and the receptor", The EMBO Journal, vol. 14:14,3395-3402 (Jul. 1995).

Dickason, Richard R., et al., "Enhanced detection of human IL-5 in biological fluids utilizing murine monoclonal antibodies which delineate distinct neutralizing epitopes", Cytokine, vol. 6:6, 647-656 (Nov. 1994).

Zhang, Ji., et al., "Mapping and characterization of the epitope(s) of Sch 55700, a humanized mAb, that inhibits human IL-5", International Immunology, vol. 11:12, 1935-1943 (Dec. 1999).

Griffiths, Andrew D., et al., "Isolation of high affinity human antibodies directly from large synthetic repertoires", The EMBO Journal, vol. 13:14, 3245-3260 (Jul. 1994).

Zabeau, Lennart., et al., "Neutralizing monoclonal antibodies can potentiate IL-5 signaling", Euro. J. Immunol., vol. 31:1087-1097 (Apr. 2001).

Rizzo, Charles A., et al., "The IL-5 receptor on human bronchus selectively primes for hyperresponsiveness", J. Allergy Clin. Immunol., vol. 109:404-409 (Mar. 2002).

Panka, et al., "Variable region framework differences result in decreased or increased affinity of variant anti-digokin antibodies", Proc. Natl. Acad. Sci. USA, vol. 85, pp. 3080-3084 (May 1988).

Rudikoff, et al., "Single amino acid substitution altering antigen-binding specificity", Proc. Natl. Acad. Sci. USA, vol. 79, pp. 1979-1983 (Mar. 1982).

Amit, et al., "Three-dimensional structure of an antigen-antibody complex at 2.8 a resolution", Science, vol. 233, pp. 747-753 (Aug. 1986).

International Search Report for International Application No. PCT/US03/09260.

Bird, Robert E., et al., "Single-Chain Antigen-Binding Proteins", Science 242:423-426 (Oct. 1988).

Egan, Robert W., et al., "Effect of Sch 55700, a Humanized monoclonal Antibody to Human Interleukin-5, on Eosinophilic Responses and Bronchial Hyperreactivity", Arzneim.-Forsch./Drug Res. 49(II), Nr. 9:779-790 (Sep. 1999).

Egan, Robert W., et al., "Inhibition of Pulmonary Eosinophilia and Hyperreactivity by Antibodies to Interleukin-5", Int. Arch Allergy Immunol. 107(1-3):321-322 (May 1995).

Fanger, Michael W., et al., "Production and Use of Anti-FcR Bispecific Antibodies", Immunomethods, 4:72-81 (Feb. 1994).

Galfre, G., et al., "Preparation of Monoclonal Antibodies: Strategies and Procedures", Methods in Enzymology, 73:3-46 (1981).

Green, Larry L., et al., "Regulation of B Cell Development by Variable Gene Complexity in Mice Reconstituted with Human Immunoglobulin Yeast Artificial Chromosomes", J. Exp. Med. 188(3):483-495 (Aug. 1998).

Green, LL., et al., "Antigen-specific human monoclonal antibodies from mice engineered with human Ig heavy and light chain YACs", Nature Genetics 7:13-21 (May 1994).

Greenfeder, Scott, et al., "Th2 cytokines and asthma. The role of interleukin-5 in allergic eosinophilic disease", Respiratory Research 2(2):71-79 (Mar. 8, 2001).

Griffiths, Andrew D., et al., "Human anti-self antibodies with high specificity from phage display libraries", The EMBO Journal 12(2):725-734 (Feb. 1993).

Holliger, Philipp, et al., "Diabodies: Small bivalent and bispecific antibody fragments", Proc Natl. Acad. Sci. USA 90:6444-6448 (Jul. 1993).

Huston, James S., et al., "Protein engineering of antibody binding sites: Recovery of specific activity in an anti-digoxin single-chain Fv analogue produced in *Escherichia coli*", Proc Natl. Acad. Sci. USA 85:5879-5883 (Aug. 1988).

Ill, Charles R., et al., "Design and construction of a hybrid immunoglobulin domain with properties of both heavy and light chain variable regions", Protein Engineering 10(8):949-957 (Aug. 1997).

Kostelny, Sheri A., et al., "Formation of a bispecific antibody by the use of leucine zippers", The Journal of Immunology 148(5):1547-1553 (Mar. 1992).

Kung, Ted T., et al., "Mechanisms of allergic pulmonary eosinophilia", J. Allergy Clin. Immunol 94(6):1217-1224 (Dec. 1994).

Martin, Franck, et al., "The affinity-selection of a minibody polypeptide inhibitor of human interleukin-6", The EMBO Journal 13(22):5303-5309 (Nov. 1994).

Mauser, Peter J., et al., "Effects of an Antibody to Interleukin-5 in a Monkey Model of Asthma", Am J Respir Crit Care Med 152:467-472 (Aug. 1995).

McCafferty, John, et al., "Phage antibodies: filamentous phage displaying antibody variable domains", Nature 348:552-554 (Dec. 1990).

Mendez, Michael J., et al., "Functional transplant of megabase human immunoglobutin loci recapitulates human antibody response in mice", Nature Genetics 15:146-156 (Feb. 1997).

Mita, Seiji, et al., "Rapid methods for purification of human recombinant interleukin-5 (IL-5) using the anti-murine IL-5 antibody-coupled immunoaffinity column", Journal of Immunological Methods 125:233-241 (1989).

Poljak, Roberto J., "Production and structure of diabodies", Structure 2(12):1121-1123 (Dec. 1994).

Songsivilai, S., et al., "Bispecific antibody: a tool for diagnosis and treatment of disease", Clin Exp. Immunol. 79:315-321 (Mar. 1990).

Traunecker, Andre, et al., "Bispecific single chain molecules (Janusins) target cytotoxic lymphocytes on HIV infected cells", The EMBO Journal 10(12):3655-3659 (Dec. 1991).

Traunecker, Andre, et al., "Janusin: New Molecular Design for Bispecific Reagents", Int. J. Cancer: Supplement 7:51-52 (1992).

* cited by examiner

METHODS FOR USING HUMAN MONOCLONAL ANTIBODIES TO INTERLEUKIN-5

This application is divisional of application Ser. No. 10/401,344 filed Mar. 27, 2003, which a non-provisional application that claims priority under 35 U.S.C. § 119(e) of provisional application No. 60/369,044 filed Mar. 29, 2002, the contents of which are hereby incorporated by reference in their entireties.

FIELD OF THE INVENTION

The present invention relates to human monoclonal antibodies and antigen-binding portions thereof that specifically bind to interleukin-5 (IL-5) and methods and compositions comprising such monoclonal antibodies or antigen-binding portions thereof.

BACKGROUND OF THE INVENTION

Eosinophils play an important role in the pathogenesis of asthma. Both asthma severity and extent of airway hyperresponsiveness correlate with numbers of blood and sputum eosinophils. Bronchial biopsy studies show that eosinophils are a prominent component of asthmatic airway inflammation and that eosinophil granule contents are present in increased concentrations in the airway lining fluid of asthmatics. These granule contents consist of a number of proteins that have direct toxic effects on airway cells through multiple mechanisms such as epithelial cell sloughing, ciliostasis, generation of oxygen radicals and injury of airway nerve fibers. Eosinophils also produce mediators that can augment mast cell histamine release. This spectrum of activities contributes directly to chronic inflammation of the bronchial airway as manifested by swelling of the airway walls and the generation of airway mucus. By facilitating the penetration of airborne agents through the damaged airway epithelium, this inflammation can directly cause increased neuronal responsiveness and smooth muscle contraction (Greenfeder et al., Respiratory Research 2:71-79, 2001).

Interleukin-5 (IL-5) is a major eosinophil mediator and a critical factor in inflammatory injury of the airways in asthma. It is produced primarily by the Th2 subset of T cells and, to a lesser extent, by other cell types including eosinophils. IL-5 is of critical importance for the maturation of eosinophils in the bone marrow and of minor importance for the chemotactic response of eosinophils. IL-5 also stimulates eosinophil activation, prolongs survival, facilitates degranulation in response to specific stimuli (such as IgA or IgG), and is generally a pro-inflammatory mediator. Increased levels of IL-5 have been measured in clinical asthma and human bronchial antigen challenge models (Greenfeder et al., Respiratory Research 2:71-79, 2001).

Asthma is currently most effectively treated by a regimen of either inhaled or oral steroids that suppress expression of a number of key mediators in asthma, including IL-5, resulting in decreased pulmonary inflammation. There are, however, perceived long-term liabilities of steroid therapy. For these reasons, direct anti-IL-5 therapy is an attractive target in the management of asthma.

Thus, it would be desirable to obtain high-affinity antibodies, particularly human anti-IL-5 antibodies, that could be used to treat Il-5 mediated pathologies in humans.

SUMMARY OF THE INVENTION

The present invention provides antibodies or antigen-binding portions thereof, that specifically bind IL-5. In certain embodiments, the antibodies or antigen-binding portions are isolated and may be polyclonal or monoclonal. In preferred embodiments, the antibodies specifically bind human IL-5. In particularly preferred embodiments, the antibodies are human monoclonal antibodies. The present invention includes antibodies that comprise a human heavy chain and/or human light chain, the entire human variable region or any portion thereof, including individual CDRs of an antibody provided herein.

In some embodiments, the heavy chain amino acid sequence of the antibodies or antigen-binding fragments thereof comprises an amino acid sequence derived from the germline amino acid sequences of a human V3-23 gene, a human D1-20 gene and a human JH4B gene. In further embodiments, the heavy chain CDR2 of the antibodies or antigen-binding fragments thereof comprises one amino acid substitution compared to the germline amino acid sequence and the heavy chain CDR3 contains two amino acid substitutions compared to the germline amino acid sequence.

In some embodiments, the light chain amino acid sequence of the antibodies or antigen-binding fragments thereof comprises an amino acid sequence derived from the germline amino acid sequences of a human VK08/018 gene and a human JK4 gene. In further embodiments, the light chain CDR1, CDR2, FR3, CDR3 and FR4 each comprise one amino acid substitution compared to the germline amino acid sequence.

In some embodiments, the antibody comprises the heavy chain amino acid sequence shown in SEQ ID NO: 2. In other embodiments, the antibody comprises a heavy chain comprising the CDR1, CDR2 and CDR3 shown in SEQ ID NOS: 8, 10, and 12, respectively. In another embodiment, the antibody heavy chain comprises a contiguous portion of the amino acid sequence shown in Table 2 from CDR1 through CDR3. In a further embodiment, the antibody heavy chain comprises the amino acid sequence of the heavy chain variable region shown in SEQ ID NO: 6. In other embodiments, any of the above-described antibodies further comprises the light chain amino acid sequence shown in SEQ ID NO: 4, or the variable region (amino acid residue 23-130 of SEQ ID NO: 4), CDR1 through CDR3 as shown in Table 3 (amino acid residue 46-119 of SEQ ID NO: 4) or CDR1 (SEQ ID NO: 14), CDR2 (SEQ ID NO: 16) and CDR3 (SEQ ID NO: 18) of the amino acid sequence of the light chain.

The antibodies or portion thereof of the invention may be an immunoglobulin G (IgG), an IgM, an IgE, an IgA or an IgD molecule. In a preferred embodiment, the human antibody is an IgG and is an IgG1, IgG2, IgG3 or IgG4 subtype. In a more preferred embodiment, the human antibody is an IgG4 subtype. In an even more preferred embodiment, the human antibody is 20.13.3. In another embodiment, the antibody or antigen-binding portion thereof is derived from an Fab fragment, an F(ab')$_2$ fragment, an F$_v$ fragment, a single chain antibody or a chimeric antibody. In another embodiment, the antibody or antigen-binding portion thereof forms part of a fusion protein.

In another aspect, the invention provides polynucleotide molecules comprising sequences encoding the heavy and light chain immunoglobulin molecules of the invention or portions thereof, particularly nucleotide sequences encoding heavy and light chain variable regions, contiguous heavy and light chain amino acid sequences from CDR1 through CDR3 and individual CDRs.

According to another object, the invention provides a human anti-IL-5 antibody or antigen-binding portion thereof that is labeled or derivatized. In one embodiment, the antibody or portion thereof is labeled with a radiolabel, an enzyme label, a toxin, a magnetic agent or a drug conjugate. In another embodiment, the antibody or portion thereof is derivatized to improve one or more of its characteristics, such as half-life, bioavailability or activity. In a preferred embodiment, the antibody or portion thereof is derivatized with polyethylene glycol, at least one methyl or ethyl group or at least one carbohydrate moiety. In another preferred embodiment, the labeled or derivatized antibody or portion thereof is used in diagnostic or therapeutic methods.

According to another object, the invention provides an anti-IL-5 antibody or antigen-binding portion thereof of the invention that is characterized by one or more of the following: inhibits or decreases IL-5-mediated inflammation, eosinophil maturation, activation, degranulation or infiltration into a tissue in vivo or in vitro, inhibits IL-5 induced hyperresponsiveness of a smooth muscle, and decreases IL-5 levels in lungs, airways or blood. In a preferred embodiment, the human antibody inhibits or decreases eosinophilic infiltration into a tissue in vivo. In a preferred embodiment, the tissue is lung or tissue lining the airways.

In accordance with another aspect, the invention provides pharmaceutical compositions and kits comprising the antibody or antigen-binding portion thereof and a pharmaceutically acceptable carrier. In a preferred embodiment, the pharmaceutical composition or kit further comprises another component, such as an imaging reagent or therapeutic agent. In preferred embodiments, the pharmaceutical composition or kit is used in diagnostic or therapeutic methods.

Another aspect of the invention comprises diagnostic methods. In one embodiment, the invention provides a method for diagnosing the presence or location of an IL-5-expressing tissue. In a preferred embodiment, the method uses a labeled antibody or portion thereof. The method may be used in vivo or in vitro. In another embodiment, there is provided a diagnostic method that comprises determining whether a human anti-IL-5 antibody inhibits or decreases eosinophilic infiltration into a tissue, e.g., the lung.

Another object of the invention comprises therapeutic methods of using a human anti-IL-5 antibody or antigen-binding portion thereof In one embodiment, a therapeutic method comprises the step of administering an effective amount of the antibody to a subject in need thereof. In a preferred embodiment, the subject is suffering from asthma, asthma exacerbations, asthma worsening episodes, chronic pneumonia, allergic rhinitis, perennial allergic rhinitis, allergic bronchopulmonary aspergillosis, hypereosinophilia, Churg-Strauss syndrome, atopic dermatitis, onchocercal dermatitis, episodic angioedema, eosinophilic myalgia syndrome, coeliac disease, eosinophilic gastroenteritis, helminth infections, Hodgkins disease, nasal polyps, Loeffler's syndrome, urticaria, hypereosinophilic bronchitis, arteritis nodosa, sinusitis, chronic sinusitis, eosinophilic esophagitis, allergic eosinophilic esophagitis, allergic conjunctivitis. In a more preferred embodiment, the method inhibits or decreases eosinophilic infiltration into the lung. The antibody or portion thereof may be administered from three times daily to once every six months, and may be administered via an intravenous, subcutaneous, intramuscular, parenteral or topical route. In another embodiment, the method is performed along with surgery or other immunotherapy. In a still further embodiment, the antibody is labeled with a radiolabel, a drug conjugate, an immunotoxin or a toxin, or is a fusion protein comprising a toxic peptide.

In another aspect, the present invention provides methods for producing an antibody of the invention or an antigen-binding portion thereof, including production by an immortalized cell, synthetic means, recombinant expression or phage display.

Another object of the invention is to provide nucleic acids encoding the heavy and/or light chain, antigen-binding portions thereof or derivatives thereof of an anti-IL-5 antibody. In a preferred embodiment, the nucleic acid molecule is derived from a cell or cell line that expresses an anti-IL-5 antibody. In a more preferred embodiment, the nucleic acid is derived from a hybridoma. In an even more preferred embodiment, the hybridoma is 20.13.3. In another embodiment, the invention provides vectors and host cells comprising the nucleic acid molecule(s). In a further embodiment, the invention provides a method of recombinantly producing the heavy and/or light chain, the antigen-binding portions thereof or derivatives thereof.

The invention also provides a method for treating a subject in need thereof with an effective amount of a nucleic acid molecule encoding the heavy and/or light chain, antigen-binding portions thereof or derivatives thereof of an anti-IL-5 antibody. In a preferred embodiment, the method is used to treat, without limitation, asthma, asthma exacerbations, asthma worsening episodes, chronic pneumonia, allergic rhinitis, perennial allergic rhinitis, allergic bronchopulmonary aspergillosis, hypereosinophilia, Churg-Strauss syndrome, atopic dermatitis, onchocercal dermatitis, episodic angioedema, eosinophilic myalgia syndrome, coeliac disease, eosinophilic gastroenteritis, helminth infections, Hodgkins disease, nasal polyps, Loeffler's syndrome, urticaria, hypereosinophilic bronchitis, arteritis nodosa, sinusitis, chronic sinusitis, eosinophilic esophagitis, allergic eosinophilic esophagitis, allergic conjunctivitis.

DETAILED DESCRIPTION OF THE INVENTION

Definitions and General Techniques

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. *Molecular Cloning: A Laboratory Manual,* 2d ed., Cold Spring Harbor Laboratory Press, Cold Spring Harbor, N.Y. (1989) and Ausubel et al., *Current Protocols in Molecular Biology*, Greene Publishing Associates (1992), and Harlow and Lane *Antibodies: A Laboratory Manual* Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The following terms, unless otherwise indicated, shall be understood to have the following meanings:

The term "polypeptide" encompasses native or artificial proteins, protein fragments and polypeptide analogs of a protein sequence. A polypeptide may be monomeric or polymeric. Preferred polypeptides in accordance with the invention comprise the human heavy chain immunoglobulin molecules and the human kappa light chain immunoglobulin molecules, as well as antibody molecules formed by combinations comprising the heavy chain immunoglobulin molecules with light chain immunoglobulin molecules, such as the κ light chain immunoglobulin molecules, as well as fragments and analogs thereof.

The term "isolated protein" or "isolated polypeptide" is a protein or polypeptide that by virtue of its origin or source of derivation (1) is not associated with naturally associated components that accompany it in its native state, (2) is free of other proteins from the same species (3) is expressed by a cell from a different species, or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

A protein or polypeptide is "substantially pure," "substantially homogeneous" or "substantially purified" when at least about 60 to 75% of a sample exhibits a single species of polypeptide. The polypeptide or protein may be monomeric or multimeric. A substantially pure polypeptide or protein will typically comprise about 50%, 60, 70%, 80% or 90% W/W of a protein sample, more usually about 95%, and preferably will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

The term "polypeptide fragment" as used herein refers to a polypeptide that has an amino-terminal and/or carboxy-terminal deletion, but where the remaining amino acid sequence is identical to the corresponding positions in the naturally-occurring sequence. Fragments typically are at least 5, 6, 8 or 10 amino acids long, preferably at least 14 amino acids long, more preferably at least 20 amino acids long, usually at least 50 amino acids long, and even more preferably at least 70 amino acids long.

The term "polypeptide analog" as used herein refers to a polypeptide that is comprised of a segment of at least 25 amino acids that has substantial identity to a portion of an amino acid sequence and that specifically binds IL-5 under suitable binding conditions. Typically, polypeptide analogs comprise a conservative amino acid substitution (or insertion or deletion) with respect to the naturally-occurring sequence. Analogs typically are at least 20 amino acids long, preferably at least 50 amino acids long or longer, and can often be as long as a full-length naturally-occurring polypeptide.

Non-peptide analogs are commonly used in the pharmaceutical industry as drugs with properties analogous to those of the template peptide. These types of non-peptide compound are termed "peptide mimetics" or "peptidomimetics". Fauchere, *J. Adv. Drug Res.* 15:29 (1986); Veber and Freidinger *TINS* p.392 (1985); and Evans et al. *J. Med. Chem.* 30:1229 (1987), which are incorporated herein by reference. Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a desired biochemical property or pharmacological activity), such as a human antibody, but have one or more peptide linkages optionally replaced by a linkage selected from the group consisting of: —CH$_2$NH—, —CH$_2$S—, —CH$_2$—CH$_2$—, —CH=CH-(cis and trans), —COCH$_2$—, —CH(OH)CH$_2$—, and —CH$_2$SO—, by methods well known in the art. Systematic substitution of one or more amino acids of a consensus sequence with a D-amino acid of the same type (e.g., D-lysine in place of L-lysine) may also be used to generate more stable peptides. In addition, constrained peptides comprising a consensus sequence or a substantially identical consensus sequence variation may be generated by methods known in the art (Rizo and Gierasch *Ann. Rev. Biochem.* 61:387 (1992), incorporated herein by reference); for example, by adding internal cysteine residues capable of forming intramolecular disulfide bridges which cyclize the peptide.

An "immunoglobulin" is a tetrameric molecule. In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as κ and λ light chains. Heavy chains are classified as μ, Δ, γ, α, or ε, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

Immunoglobulin chains exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminus to C-terminus, both light and heavy chains comprise the domains FR1, CDR1, FR2, CDR2, FR3, CDR3 and FR4. The assignment of amino acids to each domain is in accordance with the definitions of Kabat *Sequences of Proteins of Immunological Interest* (National Institutes of Health, Bethesda, Md. (1987 and 1991)), or Chothia & Lesk *J. Mol. Biol.* 196:901-917 (1987); Chothia et al. *Nature* 342:878-883 (1989).

An "antibody" refers to an intact immunoglobulin, or to an antigen-binding portion thereof that competes with the intact antibody for specific binding. Antigen-binding portions may be produced by recombinant DNA techniques or by enzymatic or chemical cleavage of intact antibodies. Antigen-binding portions include, inter alia, Fab, Fab', F(ab')$_2$, Fv, dAb, and complementarity determining region (CDR) fragments, single-chain antibodies (scFv), chimeric antibodies, diabodies and polypeptides that contain at least a portion of an immunoglobulin that is sufficient to confer specific antigen binding to the polypeptide. An Fab fragment is a monovalent fragment consisting of the VL, VH, CL and CH I domains; a F(ab')$_2$ fragment is a bivalent fragment comprising two Fab fragments linked by a disulfide bridge at the hinge region; a Fd fragment consists of the VH and CH1 domains; an Fv fragment consists of the VL and VH domains of a single arm of an antibody; and a dAb fragment (Ward et al., Nature 341:544-546, 1989) consists of a VH domain. A single-chain antibody (scFv) is an antibody in which a VL and VH regions are paired to form a monovalent molecules via a synthetic linker that enables them to be made as a single protein chain (Bird et al., Science 242:423-426, 1988 and Huston et al., Proc. Natl. Acad. Sci. USA 85:5879-5883, 1988). Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., Proc. Natl. Acad. Sci. USA 90:6444-6448, 1993, and Poljak, R. J., et al., Structure 2:1121-1123, 1994). One or more CDRs may be incorporated into a molecule either covalently or noncovalently to make it an immunoadhesin. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a particular antigen of interest.

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a "bispecific" or "bifunctional" antibody has two different binding sites. Bispecific antibodies can be produced by a variety of methods including fusion of hybridomas or linking of Fab' fragments. See, e.g., Songsivilai & Lachmann Clin. Exp. Immunol. 79: 315-321 (1990), Kostelny et al. J. Immunol. 148:1547-1553 (1992).

An "isolated antibody" is an antibody that (1) is not associated with naturally-associated components, including other naturally-associated antibodies, that accompany it in its native state, (2) is free of other proteins from the same species, (3) is expressed by a cell from a different species, or (4) does not occur in nature. Examples of isolated antibodies include an anti-IL-5 antibody that has been affinity purified using IL-5, an anti-IL-5 antibody that has been synthesized by a hybridoma or other cell line in vitro, and a human anti-IL-5 antibody derived from a transgenic mouse.

The term "human antibody" includes all antibodies that have one or more variable and constant regions derived from human immunoglobulin sequences. These antibodies may be prepared in a variety of ways, as described below.

A humanized antibody is an antibody that is derived from a non-human species, in which certain amino acids in the framework and constant domains of the heavy and light chains have been mutated so as to avoid or abrogate an immune response in humans. Alternatively, a humanized antibody may be produced by fusing the constant domains from a human antibody to the variable domains of a non-human species. Examples of how to make humanized antibodies may be found in U.S. Pat. Nos. 6,054,297, 5,886,152 and 5,877,293.

The term "chimeric antibody" refers to an antibody that contains one or more regions from one antibody and one or more regions from one or more other antibodies.

The term "$K_{off}$" refers to the off rate constant for dissociation of an antibody from the antibody/antigen complex.

The term "$K_d$" refers to the dissociation constant of a particular antibody-antigen interaction.

The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is $\leq 1$ µM, preferably $\leq 100$ nM and most preferably $\leq 10$ nM.

Fragments or analogs of antibodies or immunoglobulin molecules can be readily prepared by those of ordinary skill in the art following the teachings of this specification. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. *Science* 253:164 (1991).

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden and J. Tooze, eds., Garland Publishing, New York, N.Y. (1991)); and Thornton et at. *Nature* 354:105 (1991), which are each incorporated herein by reference.

As used herein, the twenty conventional amino acids and their abbreviations follow conventional usage. See *Immunology—A Synthesis* ($2^{nd}$ Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, s-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention.

The term "polynucleotide" as referred to herein means a polymeric form of nucleotides of at least 10 bases in length, either ribonucleotides or deoxynucleotides or a modified form of either type of nucleotide. The term includes single and double stranded forms of DNA.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence.

The term "oligonucleotide" referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g. for probes; although oligonucleotides may be double stranded, e.g. for use in the construction of a gene mutant. Oligonucleotides of the invention can be either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phoshoraniladate, phosphoroamidate, and the like. See e.g., LaPlanche et al. *Nucl. Acids Res.* 14:9081 (1986); Stec et al. *J. Am. Chem. Soc.* 106:6077 (1984); Stein et al. *Nucl. Acids Res.* 16:3209 (1988); Zon et al. *Anti-Cancer Drug Design* 6:539 (1991); Zon et al. *Oligonucleotides and Analogues: A Practical Approach*, pp. 87-108 (F. Eckstein, Ed., Oxford University Press, Oxford England (1991)); Stec et al. U.S. Pat. No. 5,151,510; Uhlmann and Peymnan *Chemical Reviews* 90:543 (1990), the disclosures of which are hereby incorporated by reference. An oligonucleotide can include a label for detection, if desired.

Unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

"Operably linked" sequences include both expression control sequences that are contiguous with the gene of interest and expression control sequences that act in trans or at a distance to control the gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. "High stringency" or "highly stringent" conditions can be used to achieve selective hybridization conditions as known in the art and discussed herein. An example of "high stringency" or "highly stringent" conditions is a method of incubating a polynucleotide with another polynucleotide, wherein one polynucleotide may be affixed to a solid surface such as a membrane, in a hybridization buffer of 6×SSPE or SSC, 50% formamide, 5× Denhardt's reagent, 0.5% SDS, 100 µg/ml denatured, fragmented salmon sperm DNA at a hybridization temperature of 42° C. for 12-16 hours, followed by twice washing at 55° C. using a wash buffer of 1×SSC, 0.5% SDS. See also Sambrook et al., supra, pp. 9.50-9.55.

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in *Atlas of Protein Sequence and Structure*, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program.

The term "corresponds to" is used herein to mean that a polynucleotide sequence is identical to all or a portion of a reference polynucleotide sequence, or that a polypeptide sequence is identical to a reference polypeptide sequence. In contrast, the term "complementary to" is used herein to mean that the complementary sequence is identical to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (*U.S.A.*) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue asis) over the comparison window. The term "percentage of sequence identity" is calculated by comparing two optimally aligned sequences over the window of comparison, determining the number of positions at which the identical nucleic acid base (e.g., A, T, C, G, U, or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more preferably at least 98 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, even more preferably at least 98 percent sequence identity and most preferably at least 99 percent sequence identity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamate-aspartate, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99% sequence identity. In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein.

As used herein, the terms "label" or "labeled" refers to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g.,$^{3}$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

The term "agent" is used herein to denote a chemical compound, a mixture of chemical compounds, a biological macromolecule, or an extract made from biological materials.

The term "pharmaceutical agent or drug" as used herein refers to a chemical compound or composition capable of inducing a desired therapeutic effect when properly administered to a patient. Other chemistry terms herein are used according to conventional usage in the art, as exemplified by The McGraw-Hill Dictionary of Chemical Terms (Parker, S., Ed., McGraw-Hill, San Francisco (1985)), incorporated herein by reference).

The term patient includes human and veterinary subjects.

Throughout this specification and claims, the word "comprise," or variations such as "comprises" or "comprising," will be understood to imply the inclusion of a stated integer or group of integers but not the exclusion of any other integer or group of integers.

Human Antibodies and Humanization of Antibodies

Human antibodies avoid certain of the problems associated with antibodies that possess mouse or rat variable and/or constant regions. The presence of such mouse or rat derived proteins can lead to the rapid clearance of the antibodies or can lead to the generation of an immune response against the antibody by a patient. Fully human anti-IL-5 antibodies are expected to minimize the immunogenic and allergic responses intrinsic to mouse or mouse-derivatized Mabs and thus to increase the efficacy and safety of the administered antibodies. The use of fully human antibodies can be expected to provide a substantial advantage in the treatment of chronic and recurring human diseases, such as inflammation and cancer, which may require repeated antibody administrations.

Methods of Producing Antibodies and Antibody-Producing Cell Lines

Immunization

In one embodiment of the instant invention, human antibodies are produced by immunizing a non-human animal comprising some or all of the human immunoglobulin locus with an IL-5 antigen or immunogenic fragment thereof. In a preferred embodiment, the non-human animal is a XenoMouse™.

The XenoMouse™ is an engineered mouse strain that comprises large fragments of the human immunoglobulin loci and is deficient in mouse antibody production. See, e.g., Green et al. Nature Genetics 7:13-21 (1994) and U.S. Pat. Nos. 5,916,771, 5,939,598, 5,985,615, 5,998,209, 6,075,181, 6,091,001, 6,114,598 and 6,130,364. See also WO 91/10741, published Jul. 25, 1991, WO 94/02602, published Feb. 3, 1994, WO 96/34096 and WO 96/33735, both published Oct. 31, 1996, WO 98/16654, published Apr. 23, 1998, WO 98/24893, published Jun. 11, 1998, WO 98/50433, published Nov. 12, 1998, WO 99/45031, published Sep. 10, 1999, WO 99/53049, published Oct. 21, 1999, WO 00 09560, published Feb. 24, 2000 and WO 00/037504, published Jun. 29, 2000.

The XenoMouse™ strains were engineered with yeast artificial chromosomes (YACs) containing 245 kb and 190 kb-sized germline configuration fragments of the human heavy chain locus and kappa light chain locus, respectively, which contained core variable and constant region sequences. Id. The XenoMouse™ produces an adult-like human repertoire of fully human antibodies, and generates antigen-specific human monoclonal antibodies (Mabs). A second generation XenoMouse™ contains approximately 80% of the human antibody repertoire through introduction of megabase sized, germline configuration YAC fragments of the human heavy chain loci and kappa light chain loci. See Mendez et al. Nature Genetics 15:146-156 (1997), Green and Jakobovits J. Exp. Med. 188:483-495 (1998), and U.S. patent application Ser. No. 08/759,620, filed Dec. 3, 1996, the disclosures of which are hereby incorporated by reference.

In another embodiment, the non-human animal comprising human immunoglobulin gene loci are animals that have a "minilocus" of human immunoglobulins. In the minilocus approach, an exogenous Ig locus is mimicked through the inclusion of individual genes from the Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described, inter alia, in U.S. Pat. Nos. 5,545,807, 5,545,806, 5,625,825, 5,625,126, 5,633,425, 5,661,016, 5,770,429, 5,789,650, 5,814,318, 5,591,669, 5,612,205, 5,721,367, 5,789,215, and 5,643,763, hereby incorporated by reference.

An advantage of the minilocus approach is the rapidity with which constructs including portions of the Ig locus can be generated and introduced into animals. However, a potential disadvantage of the minilocus approach is that there may not be sufficient immunoglobulin diversity to support full B-cell development, such that there may be lower antibody production.

In another embodiment, the invention provides a method for making anti-IL-5 antibodies from non-human, non-mouse animals by immunizing non-human transgenic animals that comprise human immunoglobulin loci. One may produce such animals using the methods described in U.S. Pat. Nos. 5,916,771, 5,939,598, 5,985,615, 5,998,209, 6,075,181, 6,091,001, 6,114,598 and 6,130,364. See. also WO 91/10741, published Jul. 25, 1991, WO 94/02602, published Feb. 3, 1994, WO 96/34096 and WO 96/33735, both published Oct. 31, 1996, WO 98/16654, published Apr. 23, 1998, WO 98/24893, published Jun. 11, 1998, WO 98/50433, published Nov. 12, 1998, WO 99/45031, published Sep. 10, 1999, WO 99/53049, published Oct. 21, 1999, WO 00 09560, published Feb. 24, 2000 and WO 00/037504, published Jun. 29, 2000. The methods disclosed in these patents may be modified as described in U.S. Pat. No. 5,994,619. In a preferred embodiment, the non-human animals may be rats, sheep, pigs, goats, cattle or horses.

In order to produce an anti-IL-5 antibody, a non-human animal comprising some or all of the human immunoglobulin loci is immunized with an IL-5 antigen or immunogenic fragment thereof. In one embodiment, the IL-5 antigen is isolated and/or purified IL-5. In a preferred embodiment, the IL-5 antigen is human IL-5. In another embodiment, the IL-5 antigen is a fragment of IL-5. In another embodiment, the IL-5 antigen is a fragment that comprises at least one epitope of IL-5. In another embodiment, the IL-5 antigen is a cell that expresses IL-5.

Immunization of animals may be done by any method known in the art. See, e.g., Harlow and Lane, *Antibodies: A Laboratory Manual*, New York: Cold Spring Harbor Press, 1990. Methods for immunizing non-human animals such as mice, rats, sheep, goats, pigs, cattle and horses are well known in the art. See, e.g., Harlow and Lane and U.S. Pat. No. 5,994,619. In a preferred embodiment, the IL-5 antigen is administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks.

Production of Antibodies and Antibody-Producing Cell Lines

After immunization of an animal with an IL-5 antigen, antibodies and/or antibody-producing cells may be obtained from the animal. In one embodiment, anti-IL-5 antibody-containing serum is obtained from the animal by bleeding or sacrificing the animal. The serum may be used as it is obtained from the animal, an immunoglobulin fraction may be obtained from the serum, or the anti-IL-5 antibodies may be purified from the serum. It is well known to one of ordinary skill in the art that serum or immunoglobulins obtained in this manner will be polyclonal. The disadvantage in using polyclonal antibodies prepared from serum is that the amount of antibodies that can be obtained is limited and the polyclonal antibody has a heterogeneous array of properties.

In another embodiment, antibody-producing immortalized cells may be prepared from the immunized animal. After immunization, the animal is sacrificed and B cells from spleen or lymph nodes are immortalized according to any means well-known in the art, including but not limited to transformation, such as with EBV or fusion with an appropriate immortalized cell line, such as myeloma cells, as is well-known in the art. See, e.g., Harlow and Lane, supra. In a preferred embodiment, the myeloma cells do not secrete immunoglobulin polypeptides (a non-secretory cell line). After fusion and antibiotic selection, the hybridomas are screened using IL-5, a portion thereof, or a cell expressing IL-5. In a preferred embodiment, the initial screening is performed using an enzyme-linked immunoassay (ELISA) or a radioimmunoassay. In a more preferred embodiment, an ELISA is used for initial screening. An example of ELISA screening is provided in WO 00/37504, herein incorporated by reference.

Anti-IL-5 antibody-producing hybridomas are selected, cloned and further screened for desirable characteristics, including robust hybridoma growth, high antibody production and desirable antibody characteristics, as discussed further below. Hybridomas may be expanded in vivo in syngeneic animals, in animals that lack an immune system, e.g., nude mice, or in cell culture in vitro. Methods of selecting, cloning and expanding hybridomas are well known to those of ordinary skill in the art.

In a preferred embodiment, the immunized animal is a non-human animal that expresses human immunoglobulin genes and B cells from spleen or lymph nodes are fused to a myeloma derived from the same species as the non-human animal. In a more preferred embodiment, the immunized animal is a Xenomouse™ and the myeloma cell line is a non-secretory mouse myeloma. In certain embodiments, the myeloma cell line is NSO-bcl2 or P3-X63-Ag8.653. See, e.g., Example 1.

In one embodiment, hybridomas are produced that produce human anti-IL-5 antibodies. In a preferred embodiment, the hybridomas are mouse hybridomas, as described above. In another preferred embodiment, the hybridomas are produced in a non-human, non-mouse species such as rats, sheep, pigs, goats, cattle or horses. In another embodiment, the hybridomas are human hybridomas, in which a human non-secretory myeloma is fused with a human cell expressing an anti-IL-5 antibody.

Nucleic Acids, Vectors, Host Cells and Recombinant Methods of Making Antibodies

Nucleic Acids

The present invention also encompasses nucleic acid molecules encoding human anti-IL-5 antibodies. In one embodiment, the nucleic acid molecule encodes a heavy and/or light chain of an intact human anti-IL-5 immunoglobulin. In a preferred embodiment, a single nucleic acid molecule encodes a heavy chain of a human anti-IL-5 immunoglobulin and another nucleic acid molecule encodes the light chain of a human anti-IL-5 immunoglobulin. In a more preferred embodiment, the encoded immunoglobulin is a human IgG.

The encoded light chain may be a λ chain or a κ chain. In an even more preferred embodiment, the encoded light chain is a κ chain.

In preferred embodiments, the nucleic acid molecule encoding the variable region of the heavy chain (VH) is derived from a human DP-47/3-11 VH gene. In various embodiments, the nucleic acid molecule encoding the VH contains no more than ten, no more than six or no more than three amino acid changes from the germline DP-47/3-11 gene. In a preferred embodiment, the nucleic acid molecule encoding the VH contains at least one amino acid change compared to the germline sequence that is identical to the amino acid change in the germline sequence from the heavy chain of the 20.13.3 antibody. In an even more preferred embodiment, the VH contains at least three amino acid changes compared to the germline sequences that are identical to at least three amino acid changes in the germline sequence from the VH of the 20.13.3 antibody.

In some embodiments, the nucleic acid molecule further comprises a nucleotide sequence derived from a human D1-20 diversity segment gene. In still other embodiments, the nucleic acid molecule further comprises a nucleotide sequence derived from a human JH4B.

Table 1 lists the nucleic acid sequences, and the corresponding amino acid sequences they encode, of the 20.13.3 antibody or portions thereof.

TABLE 1

List of sequences for Mab 20.13.3 or portions thereof

| SEQ ID NO: | SEQUENCE INFORMATION |
|---|---|
| 1 | Complete Heavy Chain DNA sequence |
| 2 | Complete Heavy Chain PROTEIN sequence |
| 3 | Complete Light Chain DNA sequence |
| 4 | Complete Light Chain Protein sequence |
| 5 | Heavy Chain variable region (V$_H$) DNA sequence |

TABLE 1-continued

List of sequences for Mab 20.13.3 or portions thereof

| SEQ ID NO: | SEQUENCE INFORMATION |
|---|---|
| 6 | Heavy Chain variable region (V$_H$) PROTEIN sequence |
| 7 | V$_H$ CDR 1 DNA sequence |
| 8 | V$_H$ CDR 1 PROTEIN sequence |
| 9 | V$_H$ CDR 2 DNA sequence |
| 10 | V$_H$ CDR 2 PROTEIN sequence |
| 11 | V$_H$ CDR 3 DNA sequence |
| 12 | V$_H$ CDR 3 PROTEIN sequence |
| 13 | V$_L$ CDR 1 DNA sequence |
| 14 | V$_L$ CDR 1 PROTEIN sequence |
| 15 | V$_L$ CDR 2 DNA sequence |
| 16 | V$_L$ CDR 2 PROTEIN sequence |
| 17 | V$_L$ CDR 3 DNA sequence |
| 18 | V$_L$ CDR 3 PROTEIN sequence |

In preferred embodiments, the nucleic acid molecule comprises a nucleotide sequence encoding the amino acid sequence of the VH of the 20.13.3 antibody at least from CDR1 through CDR3 as shown in Table 2. In another embodiment, the nucleic acid molecule comprises nucleotide sequence encoding the amino acid sequence of one or more of the CDRs of the heavy chain of the 20.13.3 antibody. In another embodiment, the nucleic acid molecule comprises a nucleotide sequence encoding the amino acid sequence of the heavy chain of the 20.13.3 monoclonal antibody shown in SEQ ID NO: 2. In another embodiment, the nucleic acid molecule comprises the nucleotide sequence encoding the heavy chain of the 20.13.3 monoclonal antibody shown in SEQ ID NO: 1. In another embodiment, the nucleic acid molecule comprises a nucleotide sequence encoding of one or more of the CDRs of the heavy chain of the 20.13.3 monoclonal antibody shown in Table 2 or shown in SEQ ID NOS: 8, 10, AND 12, respectively.

TABLE 2

AMINO ACID SEQUENCE (SEQ ID NO: 2) OF
MONOCLONAL ANTIBODY 20.13.3 HEAVY CHAIN

| | |
|---|---|
| 1 | MEFGLSWLFL VAILKGVQCE VQLLESGGGL VQPGGSLRLS CAASGFTFSS |
| | SIGNAL PEPTIDE |
| 51 | YAMSWVRQAP GKGLEWVSTI SGSGGSTYYA DSVKGRFTIS RDNSKNTLYL |
| | CDR1          CDR2 |
| 101 | QMNSLRAEDT AVYYCAKERY NWNYLHYWGQ GTLVTVSSAS TKGPSVFPLA |
| | CDR3        ▲CH1 BEGINS |
| 151 | PCSRSTSEST AALGCLVKDY FPEPVTVSWN SGALTSGVHT FPAVLQSSGL |
| 201 | YSLSSVVTVP SSSLGTKTYT CNVDHKPSNT KVDKRVESKY GPPCPSCPAP |
| 251 | EFLGGPSVFL FPPKPKDTLM ISRTPEVTCV VVDVSQEDPE VQFNWYVDGV |
| 301 | EVHNAKTKPR EEQFNSTYRV VSVLTVLHQD WLNGKEYKCK VSNKGLPSSI |
| 351 | EKTISKAKGQ PREPQVYTLP PSQEEMTKNQ VSLTCLVKGF YPSDIAVEWE |
| 401 | SNGQPENNYK TTPPVLDSDG SFFLYSRLTV DKSRWQEGNV FSCSVMHEAL |
| 451 | HNHYTQKSLS LSLGK |

The signal peptide, the first 19 amino acids, is underlined.
The complementarity determining regions 1-3 (CDR1, CDR2 and CDR3) are bolded and underlined.

In other embodiments, the above-described nucleic acid molecules can hybridize under highly stringent conditions, such as those described above, to any one of the nucleic acid sequences described above.

In other embodiments, the nucleic acid molecule encoding the variable region of the antibody light chain comprises a nucleotide sequence derived from a human 08/018 Vκ gene. Said nucleic acid molecule may contain up to ten, up to 6 or up to 3 amino acid changes from the germline 08/018 Vκ gene. In preferred embodiments, the nucleic acid molecule contains at least three amino acid changes compared to the germline Vκ sequence that are identical to the changes from germline found the 20.13.3 monoclonal antibody. In further embodiments, any of the foregoing the nucleic acid molecules further comprises a nucleotide sequence derived from a human Jκ4 joining segment gene.

In preferred embodiments, the nucleic acid molecule comprises a nucleotide sequence encoding the amino acid sequence of the light chain variable region of the 20.13.3 monoclonal antibody, at least from CDR1 through CDR3 as shown in Table 3. In other embodiments, the nucleic acid molecule comprises a nucleotide sequence encoding the amino acid sequence of one or more of the CDRs of the light chain of the 20.13.3. antibody. In another embodiment, the nucleic acid molecule comprises a nucleotide sequence encoding the amino acid sequence of the light chain of the 20.13.3 monoclonal antibody (SEQ ID NO: 4). In another embodiment, the nucleic acid molecule comprises a nucleotide sequence shown in SEQ ID NO: 3. In another embodiment, the nucleic acid molecule comprises a nucleic acid sequence that encodes the amino acid sequence of one or more of the CDRs shown in SEQ ID NOS: 14, 16, and 18.

embodiment, the nucleic acid molecule is derived from a hybridoma that has as one of its fusion partners a transgenic animal cell that expresses human immunoglobulin genes. In an even more preferred embodiment, the fusion partner animal cell is derived from a Xenomouse™ animal. In another embodiment, the hybridoma is derived from a non-human, non-mouse transgenic animal as described above.

In a preferred embodiment, the heavy chain of an anti-IL-5 antibody may be constructed by fusing a nucleic acid molecule encoding the variable domain of a heavy chain with a constant domain of a heavy chain. Similarly, the light chain of an anti-IL-5 antibody may be constructed by fusing a nucleic acid molecule encoding the variable domain of a light chain with a constant domain of a light chain. In a more preferred embodiment, the nucleic acid encoding the variable region of the heavy chain encodes the amino acid sequence of SEQ ID NO: 6, and the nucleic acid molecule encoding the variable region of the light chains encodes the amino acid sequence from residue 23-130 of SEQ ID NO: 4. The amino acid sequence from residue 139-465 of SEQ ID NO: 2 depicts the amino acid sequence of the constant region of the heavy chain of 20.13.3, and the amino acid sequence from residue 131-236 of SEQ ID NO: 4 depicts the amino acid sequence of the constant region of the light chain of 20.13.3. The nucleic acid sequence from nucleotide 415-709, 1102-1137, 1256-1585, and 1683-2002 of SEQ ID NO: 1 depicts the nucleic acid sequence encoding the constant region of the heavy chain of 20.13.3, and the nucleic acid sequence from nucleotide 391-708 of SEQ ID NO: 3 depicts the nucleic acid sequence encoding the constant region of the light chain of 20.13.3. In a preferred embodiment, the nucleic acid molecule encoding the constant domain of the heavy chain encodes the amino

TABLE 3

AMINO ACID SEQUENCE (SEQ ID NO: 4) OF
MONOCLONAL ANTIBODY 20.13.3 LIGHT CHAIN

```
  1   MDMRVPAQLL GLLLLWLSGA RCDIQMTQSP SSLSASVGDR VTITCQASQD
                                                       CDR1

51   IINYLNWYQQ KPGKAPKLLI YSASNLETRV PSRFSGSGSG TDFTFTISSL
      CDR1                  CDR2

101   QPEDIATYYC QQYDNHRPLTF GGGTKVEIRR TVAAPSVFIF PPSDEQLKSG
                  CDR3                  ▲CL1 BEGINS

151   TASVVCLLNN FYPREAKVQW KVDNALQSGN SQESVTEQDS KDSTYSLSST

201   LTLSKADYEK HKVYACEVTH QGLSSPVTKS FNRGEC
```

The signal peptide, the first 22 amino acids, is underlined.
Note: Whether the signal peptide begins "MDMRV..." or
"MRV..." is uncertain. The complementarity determining
regions 1-3 (CDR1, CDR2 and CDR3) are bolded and underlined.

In another embodiment, the nucleic acid molecule encoding a VL can hybridize under highly stringent conditions, such as those described above, to a nucleic acid sequence encoding a VL described immediately above.

A nucleic acid molecule encoding either the entire heavy or entire light chain of an anti-IL-5 antibody or the variable regions thereof may be obtained from any source that produces an anti-IL-5 antibody. In one embodiment of the invention, the nucleic acid molecules may be obtained from a hybridoma that expresses an anti-IL-5 antibody. Methods of isolating mRNA encoding an antibody are well-known in the art. See, e.g., Sambrook et al. The mRNA may be used to produce cDNA for use in the polymerase chain reaction (PCR) or cDNA cloning of antibody genes. In a preferred acid sequence from residue 139-465 of SEQ ID NO: 2, and the nucleic acid molecule encoding the constant domain of the light chain encodes the amino acid sequence from residue 131-236 of SEQ ID NO: 4. In a yet more preferred embodiment, the nucleic acid molecule encoding the constant domain of the heavy chain has the nucleic acid sequence from nucleotide 415-709, 1102-1137, 1256-1585, and 1683-2002 of SEQ ID NO: 1, and the nucleic acid molecule encoding the constant domain of the light chain has the nucleic acid sequence of the nucleic acid sequence from nucleotide 391-708 of SEQ ID NO: 3.

In another embodiment, an anti-IL-5 antibody-producing cell itself may be isolated from a non-human animal. In one embodiment, the antibody-producing cell may be derived from a transgenic animal that expresses human immunoglobulin genes and has been immunized with an IL-5 antigen. The transgenic animal may be a mouse, such as a Xenomouse™ mouse, or another non-human transgenic animal. In another embodiment, the anti-IL-5 antibody-producing cell is derived from a non-transgenic animal.

In another embodiment, the nucleic acid molecules may be used to make vectors using methods known to those having ordinary skill in the art. See, e.g., Sambrook et al. and Ausubel et al. In one embodiment, the vectors may be plasmid or cosmid vectors. In another embodiment, the vectors may be viral vectors. Viral vectors include, without limitation, adenovirus, retrovirus, adeno-associated viruses and other picoma viruses, hepatitis virus and baculovirus. The vectors may also be bacteriophage including, without limitation, M13.

The nucleic acid molecules may be used to recombinantly express large quantities of anti-IL-5 antibodies, as described below. The nucleic acid molecules may also be used to produce chimeric antibodies, single chain antibodies, immunoadhesins, diabodies, mutated antibodies and antibody derivatives, as described further below.

In one embodiment, the nucleic acid molecules encoding the variable region of the heavy (VH) and light (VL) chains are converted to full-length antibody genes. In one embodiment, such nucleic acid molecules are inserted into expression vectors already comprising sequences encoding heavy chain constant or light chain constant regions, respectively, such that the VH or VL segment is operatively linked to the CH or CL segment(s), respectively, within the vector. In another embodiment, the nucleic acid molecules encoding the VH and/or VL chains are converted into full-length antibody genes by linking the nucleic acid molecule encoding a VH chain to a nucleic acid molecule encoding a CH chain using standard molecular biological techniques. The same may be achieved using nucleic acid molecules encoding VL and CL chains. The sequences of human heavy and light chain constant region genes are known in the art. See, e.g., Kabat et al., *Sequences of Proteins of Immunological Interest*, 5th Ed., NIH Publ. No. 91-3242, 1991.

Vectors

To express the antibodies, or antibody portions of the invention, DNAs encoding partial or full-length light and heavy chains, obtained as described above, are inserted into expression vectors such that the genes are operatively linked to transcriptional and translational control sequences. Expression vectors include plasmids, retroviruses, cosmids, YACs, EBV derived episomes, and the like. The antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector. In a preferred embodiment, both genes are inserted into the same expression vector. The antibody genes are inserted into the expression vector by standard methods (e.g., ligation of complementary restriction sites on the antibody gene fragment and vector, or blunt end ligation if no restriction sites are present).

A convenient vector is one that encodes a functionally complete human CH or CL immunoglobulin sequence, with appropriate restriction sites engineered so that any VH or VL sequence can be easily inserted and expressed, as described above. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The recombinant expression vector can also encode a signal peptide that facilitates secretion of the antibody chain from a host cell. The antibody chain gene may be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

Non-Hybridoma Host Cells and Methods of Recombinantly Producing Protein

Nucleic acid molecules encoding anti-IL-5 antibodies and vectors comprising these antibodies can be used for transformation of a suitable mammalian host cell. Transformation can be by any known method for introducing olynucleotides into a host cell. Methods for introduction of heterologous olynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors. Methods of transforming cells are well known in the art. See, e.g., U.S. Pat. Nos. 4,399,216, 4,912,040, 4,740,461, and 4,959,455 (which patents are hereby incorporated herein by reference).

Mammalian cell lines available as hosts for expression are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, and a number of other cell lines. Cell lines of particular preference are selected through determining which cell lines have high expression levels. Other cell lines that may be used are insect cell lines, such as Sf9 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Further, expression of antibodies of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4.

Transgenic Animals

Antibodies of the invention can also be produced transgenically through the generation of a mammal or plant that is transgenic for the immunoglobulin heavy and light chain sequences of interest and production of the antibody in a recoverable form therefrom. In connection with the transgenic production in mammals, antibodies can be produced in, and recovered from, the milk of goats, cows, or other mammals. See, e.g., U.S. Pat. Nos. 5,827,690, 5,756,687, 5,750,172, and 5,741,957. In one embodiment, non-human transgenic animals that comprise human immunoglobulin loci are immunized with IL-5 or a portion thereof. One may produce such transgenic animals using methods described in U.S. Pat. Nos. 5,916,771, 5,939,598, 5,985,615, 5,998,209, 6,075,181, 6,091,001, 6,114,598 and 6,130,364. See also WO 91/10741, published Jul. 25, 1991, WO 94/02602, published Feb. 3, 1994, WO 96/34096 and WO 96/33735, both published Oct. 31, 1996, WO 98/16654, published Apr. 23, 1998, WO 98/24893, published Jun. 11, 1998, WO 98/50433, published Nov. 12, 1998, WO 99/45031, published Sep. 10, 1999, WO 99/53049, published Oct. 21, 1999, WO 00 09560, published Feb. 24, 2000 and WO 00/037504, published Jun. 29, 2000. In another embodiment, the transgenic animals may comprise a "minilocus" of human immunoglobulin genes. The methods disclosed above may be modified as described in, inter alia, U.S. Pat. No. 5,994,619. In a preferred embodiment, the non-human animals may be rats, sheep, pigs, goats, cattle or horses. In another embodiment, the transgenic animals comprise nucleic acid molecules encoding anti-IL-5 antibodies. In a preferred embodiment, the transgenic animals comprise nucleic acid molecules encoding heavy and light chains specific for IL-5. In another embodiment, the transgenic animals comprise nucleic acid molecules encoding a modified antibody such as a single-chain antibody, a chimeric antibody or a humanized antibody. The anti-IL-5 antibodies may be made in any transgenic animal. In a preferred embodiment, the non-human animals are mice, rats, sheep, pigs, goats, cattle or horses.

Phage Display Libraries

Recombinant anti-IL-5 human antibodies of the invention in addition to the anti-IL-5 antibodies disclosed herein can be isolated by screening of a recombinant combinatorial antibody library, preferably a scFv phage display library, prepared using human VL and VH cDNAs prepared from mRNA derived from human lymphocytes. Methodologies for preparing and screening such libraries are known in the art. There are commercially available kits for generating phage display libraries e.g., the Pharmacia Recombinant Phage Antibody System, catalog no. 27-9400-01; and the Stratagene SurfZAP™ phage display kit, catalog no. 240612). There are also other methods and reagents that can be used in generating and screening antibody display libraries (see, e.g., Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) Bio/Technology 9:1370-1372; Hay et al. (1992) Hum. Antibod. Hybridomas 3:81-85; Huse et al. (1989) Science 246:1275-1281; McCafferty et al., Nature (1990) 348:552-554; Griffiths et al. (1993) EMBO J 12:725-734; Hawkins et al. (1992) J. Mol. Biol. 226:889-896; Clackson et al. (1991) Nature 352:624-628; Gram et al. (1992) Proc. Natl. Acad. Sci. USA 89:3576-3580; Garrad et al. (1991) Bio/Technology 9:1373-1377; Hoogenboom et al. (1991) Nuc Acid Res 19:4133-4137; and Barbas et al. (1991) Proc. Natl. Acad. Sci. USA 88:7978-7982.

In a preferred embodiment, to isolate human anti-IL-5 antibodies with the desired characteristics, a human anti-IL-5 antibody as described herein is first used to select human heavy and light chain sequences having similar binding activity toward IL-5, using the epitope imprinting methods described in Hoogenboom et al., PCT Publication No. WO 93/06213. The antibody libraries used in this method are preferably scFv libraries prepared and screened as described in McCafferty et al., PCT Publication No. WO 92/01047, McCafferty et al., Nature (1990) 348:552-554; and Griffiths et al., (1993) EMBO J 12:725-734. The scFv antibody libraries preferably are screened using human IL-5 as the antigen.

Once initial human VL and VH segments are selected, "mix and match" experiments, in which different pairs of the initially selected VL and VH segments are screened for IL-5 binding, are performed to select preferred VL/VH pair combinations. Additionally, to further improve the quality of the antibody, the VL and VH segments of the preferred VL/VH pair(s) can be randomly mutated, preferably within the CDR3 region of VH and/or VL, in a process analogous to the in vivo somatic mutation process responsible for affinity maturation of antibodies during a natural immune response. This in vitro affinity maturation can be accomplished by amplifying VH and VL regions using PCR primers complimentary to the VH CDR3 or VL CDR3, respectively, which primers have been "spiked" with a random mixture of the four nucleotide bases at certain positions such that the resultant PCR products encode VH and VL segments into which random mutations have been introduced into the VH and/or VL CDR3 regions. These randomly mutated VH and VL segments can be rescreened for binding to IL-5.

Following screening and isolation of an anti-IL-5 antibody of the invention from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the invention, as described below. To express a recombinant human antibody isolated by screening of a combinatorial library, the DNA encoding the antibody is cloned into a recombinant expression vector and introduced into a mammalian host cells, as described above.

Class Switching

Another aspect of the instant invention is to provide a mechanism by which the class of an anti-IL-5 antibody may be switched with another. In one aspect of the invention, a nucleic acid molecule encoding VL or VH is isolated using methods well-known in the art such that it does not include any nucleic acid sequences encoding CL or CH. The nucleic acid molecule encoding VL or VH are then operatively linked to a nucleic acid sequence encoding a CL or CH from a different class of immunoglobulin molecule. This may be achieved using a vector or nucleic acid molecule that comprises a CL or CH chain, as described above. For example, an anti-IL-5 antibody that was originally IgM may be class switched to an IgG. Further, the class switching may be used to convert one IgG subclass to another, e.g., from IgG1 to IgG2.

Antibody Derivatives

One may use the nucleic acid molecules described above to generate antibody derivatives using techniques and methods known to one of ordinary skill in the art.

Mutated Antibodies

In another embodiment, the nucleic acid molecules, vectors and host cells may be used to make mutated anti-IL-5 antibodies. The antibodies may be mutated in the variable domains of the heavy and/or light chains to alter a binding property of the antibody. For example, a mutation may be made in one or more of the CDR regions to increase or decrease the $K_d$ of the antibody for IL-5, to increase or decrease $K_{off}$, or to alter the binding specificity of the antibody. Techniques in site-directed mutagenesis are well-known in the art. See, e.g., Sambrook et al. and Ausubel et al., supra. In a preferred embodiment, mutations are made at an amino acid residue that is known to be changed compared to germline in a variable region of an anti-IL-5 antibody. In a more preferred embodiment, one or more mutations are made at an amino acid residue that is known to be changed compared to the germline in a variable region of one of the anti-IL-5 antibodies of the invention. In another embodiment, the nucleic acid molecules are mutated in one or more of the framework regions. A mutation may be made in a framework region or constant domain to increase the half-life of the anti-IL-5 antibody. See, e.g., U.S. application Ser. No. 09/375,924, filed Aug. 17, 1999, herein incorporated by reference. A mutation in a framework region or constant domain may also be made to alter the inmuunogenicity of the antibody, to provide a site for covalent or non-covalent binding to another molecule, or to alter such properties as complement fixation. Mutations may be made in each of the framework regions, the constant domain and the variable regions in a single mutated antibody. Alternatively, mutations may be made in only one of the framework regions, the variable regions or the constant domain in a single mutated antibody.

In one embodiment, there are no greater than ten amino acid changes in either the VH or VL regions of the mutated anti-IL-5 antibody compared to the anti-IL-5 antibody prior to mutation. In a more preferred embodiment, there is no more than five amino acid changes in either the VH or VL regions of the mutated anti-IL-5 antibody, more preferably no more than three amino acid changes. In another embodiment, there are no more than fifteen amino acid changes in the constant domains, more preferably, no more than ten amino acid changes, even more preferably, no more than five amino acid changes.

Fusion Antibodies and Immunoadhesins

In another embodiment, a fusion antibody or immunoadhesin may be made which comprises all or a portion of an anti-IL-5 antibody linked to another polypeptide. In a preferred embodiment, only the variable regions of the anti-IL-5 antibody are linked to the polypeptide. In another preferred embodiment, the VH domain of an anti-IL-5 antibody are linked to a first polypeptide, while the VL domain of an anti-IL-5 antibody are linked to a second polypeptide that associates with the first polypeptide in a manner in which the VH and VL domains can interact with one another to form an antibody binding site. In another preferred embodiment, the VH domain is separated from the VL domain by a linker such that the VH and VL domains can interact with one another (see below under Single Chain Antibodies). The VH-linker-VL antibody is then linked to the polypeptide of interest. The fusion antibody is useful to directing a polypeptide to an IL-5-expressing cell or tissue. The polypeptide may be a therapeutic agent, such as a toxin, growth factor or other regulatory protein, or may be a diagnostic agent, such as an enzyme that may be easily visualized, such as horseradish peroxidase. In addition, fusion antibodies can be created in which two (or more) single-chain antibodies are linked to one another. This is useful if one wants to create a divalent or polyvalent antibody on a single polypeptide chain, or if one wants to create a bispecific antibody. In one embodiment, the fusion antibody or immunoadhesin is prepared using the variable regions from the 20.13.3 monoclonal antibody. In another embodiment, the fusion antibody or immunoadhesin is prepared using one or more CDR regions from an anti-IL-5 antibody, such as from 20.13.3.

Single Chain Antibodies

To create a single chain antibody (scFv), the VH- and VL-encoding DNA fragments are operatively linked to another fragment encoding a flexible linker, e.g., encoding the amino acid sequence $(Gly_4\text{-}Ser)_3$, such that the VH and VL sequences can be expressed as a contiguous single-chain protein, with the VL and VH regions joined by the flexible linker (see e.g., Bird et al. (1988) Science 242:423-426; Huston et al. (1988) Proc. Natl. Acad. Sci. USA 85:5879-5883; McCafferty et al., Nature (1990) 348:552-554). The single chain antibody may be monovalent, if only a single VH and VL are used, bivalent, if two VH and VL are used, or polyvalent, if more than two VH and VL are used.

In one embodiment, the single chain antibody is prepared using one or more of the variable regions from the 20.13.3 monoclonal antibody. In another embodiment, the single chain antibody is prepared using one or more CDR regions from said anti-IL-5 antibody.

Kappabodies, Minibodies, Diabodies and Janusins

In another embodiment, other modified antibodies may be prepared using anti-IL-5-encoding nucleic acid molecules. For instance, "Kappa bodies" (Ill et al., *Protein Eng* 10: 949-57 (1997)), "Minibodies" (Martin et al., *EMBO J* 13: 5303-9 (1994)), "Diabodies" (Holliger et al., *PNAS USA* 90: 6444-6448 (1993)), or "Janusins" (Traunecker et al., *EMBO J* 10: 3655-3659 (.1991) and Traunecker et al. "Janusin: new molecular design for bispecific reagents" *Int J Cancer Suppl* 7:51-52 (1992)) may be prepared using standard molecular biological techniques following the teachings of the specification.

In one embodiment, the modified antibodies are prepared using one or more of the variable regions from the 20.13.3 monoclonal antibody. In another embodiment, the modified antibody is prepared using one or more CDR regions from said anti-IL-5 antibody.

Chimeric Antibodies

In another aspect, bispecific antibodies can be generated. In one embodiment, a chimeric antibody can be generated that binds specifically to IL-5 through one binding domain and to a second molecule through a second binding domain. The chimeric antibody can be produced through recombinant molecular biological techniques, or may be physically conjugated together. In addition, a single chain antibody containing more than one VH and VL may be generated that binds specifically to IL-5 and to another molecule. Such bispecific antibodies can be generated using techniques that are well known for example, Fanger et al. *Immunol Methods* 4: 72-81 (1994) and Wright and Harris, supra. and in connection with (iii) see e.g., Traunecker et al. *Int. J. Cancer* (Suppl.) 7: 51-52 (1992). In a preferred embodiment, the chimeric antibody binds to IL-5 and to another molecule involved in promoting proliferation of eosinophils and basophils. In preferred embodiments, the other molecule is eotaxin, IL-3, or GM-CSF.

In one embodiment, the chimeric antibodies are prepared using one or more of the variable regions from the 20.13.3 monoclonal antibody. In another embodiment, the chimeric antibody is prepared using one or more CDR regions from said anti-IL-5 antibody.

Derivatized and Labeled Antibodies

An antibody or antibody portion of the invention can be derivatized or linked to another molecule (e.g., another peptide or protein). In general, the antibodies or portion thereof is derivatized such that the IL-5 binding is not affected adversely by the derivatization or labeling. Accordingly, the antibodies and antibody portions of the invention are intended to include both intact and modified forms of the human anti-IL-5 antibodies described herein. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detection agent, a cytotoxic agent, a pharmaceutical agent, and/or a protein or peptide that can mediate association of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Another type of derivatized antibody is a labeled antibody. Useful detection agents with which an antibody or antibody portion of the invention may be derivatized include fluorescent compounds, including fluorescein, fluorescein isothiocyanate, rhodamine, 5-dimethylamine-1-napthalenesulfonyl chloride, phycoerythrin, lanthanide phosphors and the like. An antibody may also be labeled with enzymes that are useful for detection, such as horseradish peroxidase, β-galactosidase, luciferase, alkaline phosphatase, glucose oxidase and the like. When an antibody is labeled with a detectable enzyme, it is detected by adding additional reagents that the enzyme uses to produce a reaction product that can be discerned. For example, when the agent horseradish peroxidase is present, the addition of hydrogen peroxide and diaminobenzidine leads to a colored reaction product, which is detectable. An antibody may also be labeled with biotin, and detected through indirect measurement of avidin or streptavidin binding. An antibody may also be labeled with a predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

An anti-IL-5 antibody may also be labeled with a radiolabeled amino acid. The radiolabel may be used for both diagnostic and therapeutic purposes. The radio-labeled anti-IL-5 antibody may be used diagnostically, for example, for determining IL-5 levels in a subject. Further, the radio-labeled anti-IL-5 antibody may be used therapeutically for treating, for example, allergic diseases characterized by pronounced eosinophilic infiltration, such as, without limitation, asthma, asthma exacerbations, asthma worsening episodes, chronic pneumonia, allergic rhinitis, perennial allergic rhinitis, allergic bronchopulmonary aspergillosis, hypereosinophilia, Churg-Strauss syndrome, atopic dermatitis, onchocercal dermatitis, episodic angiodema, eosinophilic myalgia syndrome, coeliac disease, eosinophilic gastroenteritis, helminth infections, Hodgkins disease, nasal polyps, Loeffler's syndrome, urticaria, hypereosinophilic bronchitis, arteritis nodosa, sinusitis, chronic sinusitis, eosinophilic esophagitis, allergic eosinophilic esophagitis, allergic conjunctivitis. Examples of labels for polypeptides include, but are not limited to, the following radioisotopes or radionuclides—$^3$H, $^{14}$C, $^{15}$N, $^{35}$S, $^{90}$Y, $^{99}$Tc, $^{111}$In, $^{125}$I, $^{131}$I.

An anti-Il-5 antibody may also be derivatized with a chemical group such as polyethylene glycol (PEG), a methyl or ethyl group, or a carbohydrate group. These groups may be useful to improve the biological characteristics of the antibody, e.g., to increase serum half-life or to increase tissue binding.

Characterization of Anti-IL-5 Antibodies

Class and Subclass of Anti-IL-5 Antibodies

The class and subclass of anti-IL-5 antibodies may be determined by any method known in the art. In general, the class and subclass of an antibody may be determined using antibodies that are specific for a particular class and subclass of antibody. Such antibodies are available conmmercially. The class and subclass can be determined by ELISA, Western Blot as well as other techniques. Alternatively, the class and subclass may be determined by sequencing all or a portion of the constant domains of the heavy and/or light chains of the antibodies, comparing their amino acid sequences to the known amino acid sequences of various class and subclasses of immnunoglobulins, and determining the class and subclass of the antibodies.

In one embodiment of the invention, the antibody is a polyclonal antibody. In another embodiment, the antibody is a monoclonal antibody. The antibody may be an IgG, an IgM, an IgE, an IgA or an IgD molecule. In a preferred embodiment, the antibody is an IgG and is an IgG1, IgG2, IgG3 or IgG4 subtype. In a more preferred embodiment, the anti-IL-5 antibodies are subclass IgG2. In another preferred embodiment, the anti-IL-5 antibodies are the same class and subclass as the 20.13.3 monoclonal antibody.

Binding Affinity of Anti-IL-5 to IL-5

In another aspect of the invention, the anti-IL-5 antibodies bind to IL-5 with high affinity. In one embodiment, the anti-IL-5 antibody binds to IL-5 with a $K_d$ of $1 \times 10^{-8}$ M or less. In a more preferred embodiment, the antibody binds to IL-5 with a $K_d$ or $1 \times 10^{-9}$ M or less. In an even more preferred embodiment, the antibody binds to IL-5 with a $K_d$ of $0.5 \times 10^{-9}$ M or less (e.g., a $K_d$ of $0.25 \times 10^{-9}$ M or less). In another preferred embodiment, the antibody binds to IL-5 with substantially the same $K_d$ as the 20.13.3 monoclonal antibody. In another preferred embodiment, the antibody binds to IL-5 with substantially the same $K_d$ as an antibody that comprises one or more CDRs from the 20.13.3 monoclonal antibody.

The binding affinity and dissociation rate of an anti-IL-5 antibody to IL-5 may be determined by any method known in the art. In one embodiment, the binding affinity can be measured by competitive ELISAs, RIAs, BIAcore or KinExA technology. The dissociation rate can also be measured by BIAcore or KinExA technology. In one embodiment, the binding affinity and dissociation rate are measured by surface plasmon resonance using, e.g., a BIAcore.

Identification of IL-5 Epitopes Recognized by Anti-IL-5 Antibody

The invention also provides an anti-IL-5 antibody that binds the same antigen or epitope as a human anti-IL-5 antibody. Further, the invention provides an anti-IL-5 antibody that cross-competes with a human anti-IL-5 antibody. In a preferred embodiment, the human anti-IL-5 antibody is the 20.13.3 monoclonal antibody. In another preferred embodiment, the human anti-IL-5 comprises one or more CDRs from the 20.13.3 monoclonal antibody. In a preferred embodiment, the anti-IL-5 antibody is another human antibody.

One may determine whether an anti-IL-5 antibody binds to the same antigen using a variety of methods known in the art. For instance, one may determine whether a test anti-IL-5 antibody binds to the same antigen by using an anti-IL-5 antibody to capture an antigen that is known to bind to the anti-IL-5 antibody, such as IL-5, eluting the antigen from the antibody, and then determining whether the test antibody will bind to the eluted antigen. One may determine whether an antibody binds to the same epitope as an anti-IL-5 antibody by binding the anti-IL-5 antibody to IL-5 under saturating conditions, and then measuring the ability of the test antibody to bind to IL-5. If the test antibody is able to bind to the IL-5 at the same time as the anti-IL-5 antibody, then the test antibody binds to a different epitope as the anti-IL-5 antibody. However, if the test antibody is not able to bind to the IL-5 at the same time, then the test antibody binds to the same epitope as the human anti-IL-5 antibody. This experiment may be performed using ELISA, RIA or surface plasmon resonance. In a preferred embodiment, the experiment is performed using surface plasmon resonance. In a more preferred embodiment, BIAcore is used. One may also determine whether an anti-IL-5 antibody cross-competes with an anti-IL-5 antibody. In a preferred embodiment, one may determine whether an anti-IL-5 antibody cross-competes with another by using the same method that is used to measure whether the anti-IL-5 antibody is able to bind to the same epitope as another anti-IL-5 antibody.

Light and Heavy Chain Usage

The invention also provides an anti-IL-5 antibody that comprises light chain variable sequences encoded by a human Vκ gene and a human Jκ gene. In the 20.13.3 monoclonal antibody, the κ light chains utilize a human 08/018 Vκ gene joined to a human Jκ4 gene.

In preferred embodiments, the light chain variable region of the anti-IL-5 antibodies of the invention contains the same amino acid substitutions, relative to the germline 08/018 gene amino acid sequence, as the 20.13.3 monoclonal antibody. For example, in some embodiments, the light chain variable region of the anti-IL-5 antibody may contain one or more of the amino acid substitutions relative to 08/018 germline sequence that are present in the 20.13.3 monoclonal antibody. In this manner, one can mix and match different features of antibody binding in order to alter, e.g., the affinity of the antibody for IL-5 or its dissociation rate from the antigen.

In another embodiment, the light chain variable region contains amino acid substitutions at the same positions as in the 20.13.3 monoclonal antibody, but uses different amino acids in those positions. Preferably the substitution is conservative relative to the amino acid present at that position in 20.13.3. For example, if glutamate is present in 20.13.3 at a particular position and the glutamate represents a substitution compared to germline, according to the present invention, one may conservatively substitute aspartate at that position. Similarly, if the amino acid substitution is serine, one may replace the serine with threonine.

In another preferred embodiment, the light chain comprises an amino acid sequence that is the same as the amino acid sequence of the VL of Mab 20.13.3. In another highly preferred embodiment, the light chain comprises amino acid sequences that are the same as the CDR regions of the light chain of the 20.13.3 monoclonal antibody (as shown in Table 3 and in SEQ ID NOS: 14, 16, and 18, respectively). In another preferred embodiment, the light chain comprises an amino acid sequence from at least one CDR region of the light chain of the 20.13.3 monoclonal antibody.

In another embodiment, the antibody or portion thereof comprises a lambda light chain.

The present invention also provides an anti-IL-5 antibody or portion thereof comprises a human heavy chain or a sequence derived from a human heavy chain. In one embodiment, the heavy chain amino acid sequence is derived from a human $V_H$ DP-47 gene family. In a more preferred embodiment, the heavy chain comprises no more than eight amino acid changes from germline $V_H$ DP-47, more preferably no more than six amino acid changes, and even more preferably no more than three amino acid changes.

In a preferred embodiment, the VH of the anti-IL-5 antibody contains the same amino acid substitutions, relative to the germline amino acid sequence, as Mab 20.13.3. In another embodiment, the amino acid substitutions are made in the same position as those found in the VH of Mab 20.13.3, but conservative amino acid substitutions are made rather than using the same amino acid.

In another preferred embodiment, the heavy chain comprises an amino acid sequence that is the same as the amino acid sequence of the VH of Mab 20.13.3. In another highly preferred embodiment, the heavy chain comprises amino acid sequences that are the same as the CDR regions of the heavy chain of the 20.13.3 monoclonal antibody shown in Table 2. In another preferred embodiment, the heavy chain comprises an amino acid sequence from at least one CDR region of the heavy chain of the 20.13.3 monoclonal antibody. In another preferred embodiment, the heavy chain comprises an amino acid sequence selected from SEQ ID NOS: 2, 6, 8, 10, and 12. In another preferred embodiment, the heavy chain comprises an amino acid sequence selected from SEQ ID NOS: 8, 10, and 12.

Inhibition of IL-5 Receptor Activity by Anti-IL-5 Antibody

Inhibition of IL-5 Binding to IL Receptor

In another embodiment, the invention provides an anti-IL-5 antibody that inhibits the binding of IL-5 to IL-5 receptor. In a preferred embodiment, the IL-5 receptor is human. In another preferred embodiment, the anti-IL-5 antibody is a human antibody. In another embodiment, the antibody or portion thereof inhibits binding between IL-5 and IL-5 receptor with an $IC_{50}$ of no more than 50 nM. In a preferred embodiment, the $IC_{50}$ is no more than 10 nM. In a more preferred embodiment, the $IC_{50}$ is no more than 2.0 nM, 0.5 nM, 0.25 nM, 0.1 nM, or 0.05 nM. The $IC_{50}$ can be measured by any method known in the art. Typically, an $IC_{50}$ can be measured by ELISA, RIA, or Functional Antagonism. In a preferred embodiment, the $IC_{50}$ is measured by Functional Antagonism.

Inhibition of Il-5-Mediated Cell Proliferation by Anti-IL-5 Antibody (In Vitro)

In another preferred embodiment, the invention provides an anti-IL-5 antibody that inhibits-IL-5 mediated proliferation of an IL-5-responsive cell line. In a preferred embodiment, the cell line is human. In an even more preferred embodiment, the cell line is a human eosinophil cell line or a human erythroleukemia cell line, for example, TF-1.

In a preferred embodiment, the antibody is a human antibody. In a more preferred embodiment, the antibody is the 20.13.3 monoclonal antibody or functional fragments thereof.

In certain embodiments, the anti-IL-5 antibody or functional portion thereof inhibits the proliferation of an IL-5-responsive cell line with an $IC_{50}$ value of no more than 10 nM. In preferred embodiments, the $IC_{50}$ is no more man 1 nM. In other preferred embodiments, the $IC_{50}$ is no more than 250 pM. In additional preferred embodiments, the $IC_{50}$ is no more than 100 pM. In still other preferred embodiments, the $IC_{50}$ is no more than 50 pM.

Inhibition of Eosinophil Accumulation In Vivo

In another embodiment, an anti-IL-5 antibody inhibits eosinophil accumulation in vivo. In a preferred embodiment, the antibody inhibits eosinophil accumulation by comparison to the accumulation of eosinophils in an untreated animal. In a more preferred embodiment, the antibody inhibits eosinophil accumulation by 50%. In an even more preferred embodiment, the antibody inhibits eosinophil accumulation by 75%.

In certain embodiments, the anti-IL-5 antibody therapy is conducted in conjunction with therapy with one or more additional therapeutic agents. In a preferred embodiment, the additional agent promotes further inhibition of eosinophil production, maturation, migration into blood, activation, accumulation, or infiltration into tissues in a mammal. In certain embodiments, the additional therapy comprises administration of one or more of the agents selected from the group consisting of corticosteroids, $\beta_2$ agonists, 5-LO inhibitors, LTD4 receptor antagonists, and anti-histamines. Examples of corticosteroids for such therapy include, but are not limited to beta-methasone, prednisolone and hydro-cortisone. The one or more additional therapeutic agents may be administered either separately or simultaneously with an anti-IL-5 antibody of the invention. In a preferred embodiment, the co-administration of an agent and the anti-IL-5 antibody inhibits eosinophil accumulation by at least 50%, more preferably 75%, more preferably 90% after a period of 22-24 days.

Pharmaceutical Compositions and Kits

The invention also relates to pharmaceutical compositions for the treatment of disorders, particularly allergic disorders, characterized by IL-5 mediated eosinophil production, maturation, migration into blood, activation or infiltration into tissues in a mammal. In one embodiment, said pharmaceutical composition is for the treatment of eosinophilic diseases such as, without limitation, asthma, asthma exacerbations, asthma worsening episodes, chronic pneumonia, allergic rhinitis, perennial allergic rhinitis, allergic bronchopulmonary aspergillosis, hypereosinophilia, Churg-Strauss syndrome, atopic dermatitis, onchocercal dermatitis, episodic angiodema, eosinophilic myalgia syndrome, coeliac disease, eosinophilic gastroenteritis, helminth infections, Hodgkins disease, nasal polyps, Loeffler's syndrome, urticaria, hypereosinophilic bronchitis, arteritis nodosa, sinusitis, chronic sinusitis, eosinophilic esophagitis, allergic eosinophilic esophagitis and allergic conjunctivitis.

The anti-IL-5 antibodies of the invention can be incorporated into pharmaceutical compositions suitable for administration to a subject. Typically, the pharmaceutical composition comprises an antibody or a functional fragment thereof of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable substances such as wetting or minor amounts of auxiliary substances such as wetting or emulsifying agents, preservatives or buffers, which enhance the shelf life or effectiveness of the antibody or antibody portion.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the anti-IL-5 antibody in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies or antigen-binding fragments of the present invention can be administered by a variety of methods known in the art, although for many therapeutic applications, the preferred route/mode of administration is subcutaneous, intramuscular, intravenous or infusion. As will be appreciated by the skilled artisan, the route and/or mode of administration will vary depending upon the desired results.

In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

In certain embodiments, the anti-IL-5 antibody or antigen-binding fragments of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, an anti-IL-5 antibody of the invention is coformulated with and/or coadministered with one or more additional therapeutic agents. These agents include, without limitation, antibodies that bind other targets (e.g., antibodies that bind one or more growth factors or cytokines or their cell surface receptors), agents that reduce IL-5 production or activity, such as IL-5 binding proteins, antisense oligonucleotides against IL-5 or IL-5 receptor, peptide analogues that block IL-5 receptor activation, soluble IL-5 receptor, glucocorticoids and cyclosporin, and agents that inhibit eosinophil production, maturation, survival, activation, or migration from the bone marrow, such as corticosteroids. Such combination therapies may require lower dosages of the anti-IL-5 antibody and/or the co-administered agents, thus avoiding possible toxicities or complications associated with the various monotherapies.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody or antibody portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the antibody and the particular therapeutic or prophylactic effect to be achieved, and (b) the limitations inherent in the art of compounding such an antibody for the treatment of sensitivity in individuals.

An exemplary, non-limiting range for a therapeutically or prophylactically effective amount of an antibody or antibody portion of the invention is 0.1-100 mg/kg, more preferably 0.1-50 mg/kg, more preferably 0.1-20 mg/kg, and even more preferably 1-10 mg/kg (e.g., at 0.3, 1, or 3 mg/kg). It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Another aspect of the present invention provides kits comprising the anti-IL-5 antibodies or antigen-binding fragments and the pharmaceutical compositions comprising these antibodies. A kit may include, in addition to the antibody or pharmaceutical composition, diagnostic or therapeutic agents. A kit may also include instructions for use in a diagnostic or therapeutic method. In a preferred embodiment, the kit includes the antibody or a pharmaceutical composition thereof and a diagnostic agent that can be used in a method described below. In another preferred embodiment, the kit includes the antibody or a pharmaceutical composition thereof and one or more therapeutic agents that can be used in a method described below.

Diagnostic Methods of Use

The anti-IL-5 antibodies of the invention or antigen-binding fragments thereof may be used to detect IL-5 in a biological sample. The anti-IL-5 antibodies may be used in a conventional immunoassay, including, without limitation, an ELISA, an RIA, FACS, tissue immunohistochemistry, Western blot or immunoprecipitation. The anti-IL-5 antibodies of the invention may be used to detect IL-5 from humans. In another embodiment, the anti-IL-5 antibodies may be used to detect IL-5 from Old World primates such as cynomologous and rhesus monkeys, chimpanzees and apes. The invention provides a method for detecting IL-5 in a biological sample comprising contacting a biological sample with an anti-IL-5 antibody of the invention antigen-binding fragments thereof and detecting the antibody bound to IL-5, to detect the IL-5 in the biological sample. In one embodiment, the anti-IL-5 antibody is directly labeled with a detectable label. In another embodiment, the anti-IL-5 antibody (the first antibody) is unlabeled and a second antibody or other molecule that can bind the anti-IL-5 antibody is labeled. As is well known to one of skill in the art, a second antibody is chosen that is able to specifically bind the specific species and class of the first antibody. For example, if the anti-IL-5 antibody is a human IgG, then the secondary antibody may be an anti-human-IgG. Other molecules that can bind to antibodies include, without limitation, Protein A and Protein G, both of which are available commercially, e.g., from Pierce Chemical Co.

Suitable labels for the antibody or secondary have been disclosed supra, and include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}I$, $^{131}I$, $^{35}S$ or $^{3}H$.

In an alternative embodiment, IL-5 can be assayed in a biological sample by a competition immunoassay utilizing IL-5 standards labeled with a detectable substance and an unlabeled anti-IL-5 antibody. In this assay, the biological sample, the labeled IL-5 standards and the anti-IL-5 antibody are combined and the amount of labeled IL-5 standard bound to the unlabeled antibody is determined. The amount of IL-5 in the biological sample is inversely proportional to the amount of labeled IL-5 standard bound to the anti-IL-5 antibody.

One may use the immunoassays disclosed above for a number of purposes. In one embodiment, the anti-IL-5 antibodies or fragments may be used to detect IL-5 in a sample, particularly a biological sample.

Therapeutic Methods of Use

In another embodiment, the invention provides a method for inhibiting IL-5 activity by administering an anti-IL-5 antibody of the invention or an antigen-binding fragment thereof to a patient in need thereof. Any of the types of antibodies described herein may be used therapeutically. In a preferred embodiment, the anti-IL-5 antibody is a human antibody. In another preferred embodiment, the IL-5 is human and the patient is a human patient. Alternatively, the antibody or fragment may be administered to a non-human mammal expressing an IL-5 with which the antibody cross-reacts (i.e. a primate, cynomologous or rhesus monkey) for veterinary purposes or as an animal model of human disease. Such animal models may be useful for evaluating the therapeutic efficacy of antibodies of this invention.

As used herein, the term "a disorder in which IL-5 activity is detrimental" is intended to include diseases and other disorders in which the presence of IL-5 in a subject suffering from the disorder has been shown to be or is suspected of being either responsible for the pathophysiology of the disorder or a factor that contributes to a worsening of the disorder. Accordingly, a disorder in which IL-5 activity is detrimental is a disorder in which inhibition of IL-5 activity is expected to alleviate the symptoms and/or progression of the disorder. Such IL-5 mediated disorders include, but are not limited to, allergic disorders, particularly allergic disorders of the skin and pulmonary tissues and pulmonary inflammation. Such disorders may be evidenced, for example, by an increased number of eosinophils and/or basophils in the bone marrow, blood or other tissues, or in bronchoalveolar lavage (BAL) fluid. In particular, such disorders may be characterized by pulmonary or cutaneous eosinophilia, bronchial hyper-responsiveness, eosinophil accumulation in lung tissue, perivascular and/or peribronchial regions, damage to airway epithelium, interstitial airway edema, increased mucus secretion in bronchi or broncho-constriction. Alternatively, pathological IL-5 activity may be evidenced by one or more of increased eosinopoiesis in the bone marrow, increased eosinophil survival, increased eosinophil adhesion to endothelial cells and enhanced eosinophil cytotoxic activity.

In a preferred embodiment, an anti-IL-5 antibody of the invention or an antigen-binding fragment thereof may be administered to a patient suffering from inflammation, including allergic disease characterized by pronounced eosinophilic infiltration, such as nasal rhinitis, nasal polyps, asthma, idiopathic eosinophilic syndromes, and atopic dermatitis. In an even more preferred embodiment, the anti-IL-5 antibody is administered to a patient who has a chronic pulmonary inflammation. In a highly preferred embodiment, the method causes the inflammation to become less severe or to disappear.

In another preferred embodiment, an anti-IL-5 antibody may be administered to a patient having increased levels of eosinophils in bone marrow, blood or other body tissues. Increased eosinophil presence is known in the art to be associates with diseases such as, without limitation, asthma, asthma exacerbations, asthma worsening episodes, chronic pneumonia, allergic rhinitis, perennial allergic rhinitis, allergic bronchopulmonary aspergillosis, hypereosinophilia, Churg-Strauss syndrome, atopic dermatitis, onchocercal dermatitis, episodic angiodema, eosinophilic myalgia syndrome, coeliac disease, eosinophilic gastroenteritis, helminth infections, Hodgkins disease, nasal polyps, Loeffler's syndrome, urticaria, hypereosinophilic bronchitis, arteritis nodosa, sinusitis, chronic sinusitis, eosinophilic esophagitis, allergic eosinophilic esophagitis, allergic conjunctivitis. In a preferred embodiment, the anti-IL-5 antibody of the invention or an antigen-binding fragment thereof is administered to a patient with asthma. In an even more preferred embodiment, the method prevents or reduces the severity of the disease.

The antibody or fragment may be administered from about three times daily to about once every six months, and preferably may be administered via an oral, mucosal, buccal, intranasal, inhalable, intravenous, subcutaneous, intramuscular, parenteral, intratumor or topical route. The antibody may also be administered continuously via a minipump. The antibody generally will be administered for as long as the disease condition is present, provided that the antibody causes the condition to stop worsening or to improve. The antibody will generally be administered as part of a pharmaceutical composition as described szupra. The antibody may also be administered prophylactically in order to prevent allergic inflammation and/or eosinophilic infiltration from occurring. This may be especially useful in patients that have been shown to have a higher risk of developing an IL-5 mediated or eosinophil-mediated condition.

Gene Therapy

The nucleic acid molecules of the instant invention may be administered to a patient in need thereof via gene therapy. The therapy may be either in vivo or ex vivo. In a preferred embodiment, nucleic acid molecules encoding both a heavy chain and a light chain are administered to a patient. In a more preferred embodiment, the nucleic acid molecules are administered such that they are stably integrated into the chromosome of B cells because these cells are specialized for producing antibodies. In a preferred embodiment, precursor B cells are transfected or infected ex vivo and re-transplanted into a patient in need thereof. In another embodiment, precursor B cells or other cells are infected in vivo using a virus known to infect the cell type of interest. Typical vectors used for gene therapy include liposomes, plasmids, or viral vectors, such as retroviruses, adenoviruses and adeno-associated viruses. After infection either in vivo or ex vivo, levels of antibody expression may be monitored by taking a sample from the treated patient and using any immunoassay known in the art and discussed herein.

In a preferred embodiment, the gene therapy method comprises the steps of administering an effective amount of an isolated nucleic acid molecule encoding the heavy chain or the antigen-binding portion thereof of the human antibody and expressing the nucleic acid molecule. In another embodiment, the gene therapy method comprises the steps of administering an effective amount of an isolated nucleic acid molecule encoding the light chain or the antigen-binding portion thereof of the human antibody and expressing the nucleic acid molecule. In a more preferred method, the gene therapy method comprises the steps of administering an effective amount of an isolated nucleic acid molecule encoding the heavy chain or the antigen-binding portion thereof of the human antibody and an effective amount of an isolated nucleic acid molecule encoding the light chain or the antigen-binding portion thereof of the human antibody and expressing the nucleic acid molecules. The gene therapy method may also comprise the step of administering another agent that has similar therapeutic effects as the antibody or functional fragment thereof, such as those enumerated, supra.

In order that this invention may be better understood, the following examples are set forth. These examples are for purposes of illustration only and are ot to be construed as limiting the scope of the invention in any manner.

EXAMPLE 1

Generation of Hybridomas Producing Anti-IL-5 Antibody

Antibodies of the invention were prepared, selected, and assayed as follows:

Immunization and Hybridoma Generation

A total of 288 IgG2 or IgG4 XenoMice™ divided into groups of 15 to 20 mice aged 8 to 15 weeks were immunized according to the schedule shown in Table 4 below.

For base of tail (bot) immunizations, human IL-5 was emulsified in complete Freund's adjuvant (CFA) for the first immunization and in incomplete Freund's adjuvant (IFA) for subsequent immunizations at the doses and times indicated above. (For IL-5 sequence information, see European Patent Application publication number EP0267779.) For footpad (FP) immunization, the antigen was emulsified in Ribi adjuvant. Some animals (group 7) received antigen through both bot and intraperitonealy (ip) in CFA or Ribi. Group 8 received antigen in the form of conjugate in which human IL-5 was chemically conjugated to a mouse anti-CD3 antibody.

Spleen and/or lymph node cells from immunized mice were fused with either the non-secretory myeloma P3-X63-Ag8.653 cell line (ATCC, Rockville, Md.) or the myeloma NSO-bcl2 cell line (B. Diamond, Albert Einstein College of Medicine, NY), as previously described (Galfre and Milstein, *Methods Enzymol.* 73:3-46, 1981). Cultures were regularly examined for hybrid cell growth, and supernatants from those wells containing hybridomas were collected for a primary ELISA screen for the presence of human IgG/kappa specific for IL-5.

IL-5 Binding Assay

ELISA plates were coated with 50 μl/well IL-5 antigen at 2 μg/ml in Coating buffer (0.1 M carbonate buffer, pH 9.6 and 8.4 g/l NaHCO3 (MW 84)) and incubated at 4° C. overnight or at 37° C. for 2 hours. The plates were washed with washing buffer (0.05% Tween 20 in PBS) three times, blocked with 200 μl/well of blocking buffer (0.5% BSA, 0.1% Tween 20, 0.01% Thimerosal in 1×PBS) for 1 hour at room temperature, and washed three more times with washing buffer. Fifty μl/well of sample (or controls) was added to the wells and incubated at room temperature for 2 hours. After three washes with washing buffer, 100 μl/well of detecting antibody goat anti-huIgGfc-HRP (Caltag, cat.#H10507) (and GT anti-hkappa-HRP in secondary screening) was added to each well and incubated for 1 hour at room temperature. The plates were washed and 100 μl of developing solution (10 ml substrate buffer, 7.14 g/l citric acid and 16.96 g/l dibasic sodium phosphate), 10 mg o-phenylenediamine (Sigma, cat. no. P-7288), and 10 μl 30% $H_2O_2$) was added to each well. After approximately 10 minutes, stop solution (2 M $H_2SO_4$) was added to each well and the plates were analyzed using an ELISA plate reader at a wavelength of 492 nm. Positive cultures were transferred to 48-well plates and were subsequently transferred to 24-well plates after reaching confluence.

A total of 116 hybridomas producing antibodies reactive with IL-5 were obtained, of which 7 were IgG2 and 109 were

TABLE 4

Immunization Schedules

| | # mice | | | | | dose | | | |
|---|---|---|---|---|---|---|---|---|---|
| Grp | Gamma-2 | Gamma 4 | Fusion # | immunogen | route | first | others | Interval | # doses |
| 1 | 10 | 15 | SP1-SP2 | in CFA/IFA | bot | 20 ug | 10 ug | 2-3 weeks | 4 |
|   | 10 | 13 | SP3-SP6 |   |   |   |   |   | 7 |
| 2 | 10 | 15 | SP7-SP10 | in CFA/IFA | bot | 20 ug | 10 ug | 2-3 weeks | 4 |
|   | 10 | 15 | SP11-SP14 |   |   |   |   |   | 7 |
| 3 | 10 | 15 | SP15-SP18 | in CFA/IFA | bot | 20 ug | 10 ug | 2-3 weeks | 4 |
|   | 10 | 15 | SP19-SP20 |   |   |   |   |   | 7 |
| 4 | 20 | 20 | SP23-SP24 | in CFA/IFA | bot | 20 ug | 10 ug | 4-5 weeks | 7 |
| 5 | 10 | 20 | SP33-SP35 | in CFA/IFA | bot | 20 ug | 10 ug | 3-4 weeks | 8 |
| 6 | 10 | 10 | SP21-SP22 | in Ribi | fp | 20 ug | 10 ug | 3-4 days | 7 |
| 7 | 20 | 20 | SP25-SP30 | Ribi or CFA | bip | 20 ug | 10 ug | 2-3 weeks | 5 |
| 8 | 10 | 10 | SP31-SP32 | IL5-anti m-CD3 | bot | 20 ug | 20 ug | 2-3 weeks | 4 |

IgG4. The disproportionate prevalence of IgG4 antibodies is thought to be related to an effect of IL-5 on class switching. Of the 116 hybridomas producing IL-5 specific antibodies, an IgG4/kappa hybridoma designated 20.13 was selected for further characterization based on their strong neutralization activity comparable to that of a mouse IgG control antibody (39D10 from Schering-Plough).

EXAMPLE 2

Proliferation Assay for Determining Biologically Functional Antibodies

Affinity purified hybridoma ascites and supernatants were used for a quantitative functional assay for neutralization of IL-5-induced proliferation of TF1 cells (DNAX). Briefly, recombinant human IL-5 was diluted in 1% FBS RPMI-1640 culture media to a final concentration of 1.0 ng/ml, and the control antibody, 39D10 (Schering-Plough) was diluted to a final concentration of 1.0 µg/ml with IL-5 media. Either the IL-5 solution or IL-5 plus 39D10 solution was added to wells of 96-well plates. Control wells contained only media or only IL-5.

TF1 cells were washed twice with RPMI-1640 media and resuspended to a final concentration of $2.5 \times 10^5$ TF1 cells per ml in FBS culture media. 100 µl of the cell suspension was added to each well and incubated for 48-56 hours at 37° C. and 5% $CO_2$. After 48 hours, 20 µl of Alamar Blue was added to each well and incubated overnight. The plates were analyzed using a FluoroCount™ plate reader at an excitation wavelength of 530 nm, emission wavelength of 590 nm, and PMT of 600 volts.

Results of studies using antibody 20.13.3, purified from either acites or supernatants, show that 20.13.3 effectively blocked cell proliferation induced by IL-5.

EXAMPLE 3

Determination of Neutralization $IC_{50}$

Mab 20.13.3 was tested in the TF-1 anti-proliferation assay against both human and murine IL-5 (Egan et al. Drug Res. 49:779-790 (1999)). Briefly, 50 µl of assay medium (RPMI 1640 supplemented with 1% glutamine, 1% pen/strep solution, 0.1% mercaptoethanol, 0.05% fungizone and 1% fetal bovine serum) was added to wells of a 96-well culture plate. Varying concentrations of Mab 20.13.3 were added to the wells and incubated at room temperature for 30 minutes. Twenty microliters (20 µl) of human or murine IL-5 (12 ng/ml) was added to each well (except negative controls). TF-1 cells were prepared at a concentration of $5 \times 10^5$ cells per ml, and 30 µl aliquots of cell suspension were added to all wells. The plates were incubated for 44-48 hours at 37° C. and 5% $CO_2$. 25 µl of a 5 mg/ml MTT solution was then added to each well and incubated for another 6 hours. 100 µl of a 10% SDS solution was added to each well and the plastes were incubated overnight. The plates were analyzed on a UV MAX™ spectrophotometer. Results indicate that in the assay, Mab 20.13.3 exhibits IC50 values of 250 pM and 380 pM against human and murine IL-5, respectively.

EXAMPLE 4

In Vivo Functional Assay

An anti-IL-5 antibody of the invention was evaluated in a mouse model of antigen induced pulmonary inflammation (Kung et al 1994). Briefly, mice sensitized with ovalbumin (OVA) were dosed with either saline, Mab 20.13.3 at 5, 1, 0.5, or 0.1 mg/kg s.c., or a positive control murine anti-IL-5 mAb, TRFK-5 (Schering Plough Research Institute; Mita et al., J. Immunol. Methods 125:233 (1987)) at 1 mg/kg i.p 2 hrs prior to challenge with aerosolized OVA. Bronchoalveolar lavage (BAL) fluid was collected 24 hrs post challenge and cellularity was determined. TRFK-5 produced a significant decrease in all parameters. Mab 20.13.3 significantly inhibited total cells and eosinophils in the BAL at 5, 1 and 0.5 mg/kg.

The duration of activity of anti-IL-5 antibodies of the invention was evaluated in the above-described model. Mice sensitized with ovalbumin (OVA) were dosed with either saline or Mab 20.13.3 at 5 and 1 mg/kg s.c. 2 hrs, 2 weeks, 4 weeks, 6 weeks, 8 weeks or 12 weeks prior to challenge with aerosolized OVA. Bronchoalveolar lavage fluid was collected 24 hrs post challenge and cellularity was determined. Blood samples were taken at the time of BAL collection for pharmacokinetic analysis. The 5 and 1 mg/kg doses of Mab 20.13.3 significantly inhibited total cells and eosinophils in the BAL when given 2 hrs and 13 days prior to OVA challenge. Mab 20.13.3 significantly inhibited total cells and eosinophils in the BAL when given 4w prior to challenge only at the 5 mg/kg dose. Inhibition was no longer observed when Mab 20.13.3 was dosed 6w-12w prior to challenge.

We evaluated Mab 20.13.3 in a cynomolgus monkey model of antigen induced pulmonary inflammation (Mauser et al 1995). Briefly, nine monkeys naturally sensitive to *Ascaris sutum* were first sham treated with vehicle (subcutaneous saline) and 18 hrs later challenged with aerosolized *Ascaris suum* (antigen). Twenty-four hours after *Ascaris* challenge, a BAL fluid sample was collected and a peripheral blood sample was obtained. The cellular content of the BAL and blood samples were determined.

Three weeks later, the nine monkeys were dosed with Mab 20.13.3 at 0.3 mg/kg s.c. Eighteen hours later, the monkeys were challenged with aerosolized *Ascaris suum* and a BAL sample was collected 24 hrs later. Blood samples were taken before and at selected times after administration of *Ascaris suum*. *Ascaris suum* challenge was repeated 4 and 8 weeks after the initial dosing with Mab 20.13.3 and the cell content in the BAL fluid was analyzed before and 24 hours after each *Ascaris* challenge. Mab 20.13.3 significantly reduced the antigen-induced accumulation of eosinophils in the BAL 4w after dosing with a trend towards reduced levels (55% reduction) 8w after dosing. Mab 20.13.3 significantly reduced the number of eosinophils in the peripheral blood 42h, 2w, 4w, 8w and 12w after dosing with levels returning to near pre-dosing levels by 14w.

EXAMPLE 5

Structural Analysis of the Fully Human Anti-IL-5 Monoclonal Antibodies

To analyze the structure of antibodies produced in accordance with the invention, we cloned and sequenced nucleic acids encoding heavy and light chain fragments from hybridomas producing anti-IL-5 monoclonal antibodies. We analyzed all sequences by alignments to the "V BASE sequence directory" (Tomlinson et al., MRC Centre for Protein Engineering, Cambridge, UK) using MacVector and Geneworks software programs.

To clone the cDNA encoding monoclonal antibody 20.13.3, we isolated RNA from approximately $1 \times 10^6$ hybridoma cells by the RNAzol (Tel-Test, INC.) method. We reverse transcribed the mRNA using oligo-dT(18) and the Advantage™ RT/PCR kit (Clonetech). We used the following primers to amplify the cDNA.

| Primer name | Primer Sequence |
|---|---|
| Light Chain Sense: vk018-Eco | 5'-GGAAGAATTCACCCTGTGCAGGAGTCAGTCC-3' (SEQ ID NO: 19) |
| LC Anti-sense: ckp2-Apa | 5'-TGAGATCGAGGGCCCCTTCTCCCTCTAACACTCTCC-3' (SEQ ID NO: 20) |
| Heavy Chain Sense: v3-23-Eco | 5'-CCGGAATTCCAGAGAGAACTCACCATGGAGTTTG-3' (SEQ ID NO: 21) |
| Heavy Chain Anti-sense: Jh4/5-Nhe | 5'-GAGAGAGAGCTAGCTGAGGAGACGGTGACCAGGGTTCCCT-3' (SEQ ID NO: 22) |

20.13.3 cDNA light chain PCR products were electrophoreised in 1% agarose/TAE gels and ~760 bp band excised and purified with sephaglas beads (Amersham) and subcloned into PCR TOPO2.1 vector (Invitrongen). cDNA inserts were sequenced with dye primer sequencing kit (Applied Biosystems) with vk018-Eco and ckp2-Apa primers. Sequence analysis was performed using SeqEd and GeneWorks software. EcoRI/ApaI fragments isolated from identified plasmids were cloned into the expression vector pManuKappa.

20.13.3 heavy chain PCR products were digested with EcoRI(NheI, electrophoreised in 1% agarose/TAE gels and 435 bp band excised and purified with sephaglas (Amersham) and subcloned into pManuGamma4. Clones were sequenced with dye primer sequencing kit (Applied Biosystems) with v3023-Eco and Jh4-Nhe primers.

For each clone, we verified the sequence on both strands in at least three reactions.

Gene Utilization Analysis

Table 5 sets forth the gene utilization by the 20.13.3 hybridoma in accordance with the invention.

TABLE 5

Heavy and Light Chain Gene Utilization

| | Heavy Chain | | | Kappa Light Chain | |
|---|---|---|---|---|---|
| Clone | VH | D | JH | VK | JK |
| 20.13.3 | (3-23) DP-47 | D1-20 | JH4B | O8/O18 | JK4 |

Mutation Analysis

As will be appreciated, gene utilization analysis provides only a limited overview of antibody structure. As the B-cells in XenoMouse™ animals stocastically generate V-D-J heavy or V-J kappa light chain transcripts, there are a number of secondary processes that occur, including, without limitation, somatic hypermutation,—additions, and CDR3 extensions. See, for example, Mendez et al., *Nature Genetics* 15:146-156 (1997) and International Patent Publication WO98/24893, published Oct. 11, 1998. Accordingly, to further examine antibody structure, we generated predicted amino acid sequences of the antibodies from the cDNAs obtained from the clones.

The heavy chain variable domain of Mab 20.13.3 contains three amino acid substitutions compared to germline—one in the CDR2 and two in CDR3. The light chain variable domain of Mab 20.13.3 contains five mutations from germline, one each in CDR1, CDR2, FR3, CDR3 and FR4.

It will be appreciated that many of the above-identified amino acid substitutions or insertions exist in close proximity to or within a CDR. Such substitutions would appear to bear some effect upon the binding of the antibody to the IL-5 molecule. Further, such substitutions could have significant effect upon the affinity of the antibodies.

EXAMPLE 6

Determination of Affinity Constants ($K_d$) of Fully Human Anti-IL-5 Monoclonal Antibody by Kinetic Exclusion Assay The equilibrium dissociation constant (Kd) for human monoclonal antibody 20.13.3 was determined using the KinExA 3000™ instrument (Sapidyne Instruments Inc.). The KinExA uses the principle of the Kinetic Exclusion Assay method based on measuring the concentration of uncomplexed antibody in a mixture of antibody, antigen and antibody-antigen complex. The concentration of free antibody is measured by exposing the mixture to a solid-phase immobilized antigen for a very brief period of time. In practice, this is accomplished by flowing the solution phase antigen-antibody mixture past antigen coated particles trapped in a flow cell. Data, generated by the instrument are analyzed using custom software. Equilibrium constants are calculated using a mathematical theory based on the following assumptions:

1. The binding follows the reversible binding equation for equilibrium:

$$K_{on}[Ab][Ag]=K_{off}[Ab\,Ag];$$

2. Antibody and antigen bind 1:1, and total antibody equals antigen-antibody complex plus free antibody; and
3. Instrument signal is linearly related to free antibody concentration.

All experimental procedures were performed according to the KinExA 3000™ Manual. All runs were done in duplicate. The following table show the assay 20 conditions for the standard $K_d$ runs at Ab concentrations of 0.1 nM and 0.01 nM, respectively:

| | Ab concentration | |
|---|---|---|
| | 0.1 nM | 0.01 nM |
| Sample volume: | 500 ul | 2000 ul |
| Sample flow rate: | 0.25 ml/min | 0.25 ml/min |
| Label volume: | 500 ul | 500 ul |
| Label flow rate: | 0.25 ml/min | 0.25 ml/min |
| Highest Ag concentration: | 500 pM | 40 pM |
| Lowest Ag concentration: | 0.5 pM | 0.07 pM |

In each assay, two-fold serial dilutions of the antigen were prepared and mixed with the antibody at constant concentration. The mixture was incubated for 2 hours at room temperature to equilibrate.

Materials used in the above assays were: Mab 20.13.3; recombinant human IL_5 (rhIL-5) (available from Sigma (Cat# I 5273), R&D Systems (Cat# 205-IL-005), Amersham (Cat# ARM19005), and Calbiochem (Cat# 407641)); PMMA particles, 8 micron (Sapidyne, Cat No.440198); Neutravidin (Pierce, Cat No.31000); EZ-link TFP PEO-Biotin (Pierce, Cat No. 21219); Biotinylated rhIL-5 (Biotin/protein ratio: 19/1); and Cy5 conjugated Goat anti-HuIgG (H+L) (Jackson Immunoresearch Laboratories Cat. No 109-175-003). PMMA particles were coated with biotinylated rhIL-5 according to Sapidyne "Protocol for coating PMMA particles with biotinylated ligands having short or nonexistent linker arms". For biotinylation of rhIL-5 EZ-link TFP PEO-biotin was used according to manufacturer's recommendations (Pierce bulletin 0874). Biotin/protein ratio was estimated using the HABA assay (Pierce bulletin 0212).

Dual Curve analysis (0.1 and 0.01 nM Antibody concentrations) in the "Standard mode" (see KinExA 3000™ Manual for an explanation of Dual Curve data analysis methods) generated good best fit curve for Kd with clear minimum. The calculated Kd value for Mab 20.13.3 for this method of analysis was $1.5 \times 10^{-11}$ M. The Mab 20.13.3 Kd calculated by the Dual Curve (Unknown Antigen) method was $1.95 \times 10^{-11}$ M, which was realizably close to the Kd obtained by the Dural Curve (Standard) method. The antibody molecular weight used for calculation was 150 Kda.

The kinetic analyses indicates that the antibodies prepared in accordance with the invention possess high affinities for human IL-5.

Throughout this specification and claims, the word "comprise," or variations such as "comprises" or "comprising" will be understood to imply the inclusion of a stated integer or group of integers but not the exclusion of any other integer or group of integers.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A method for treating a condition or disorder in which IL-5 activity is detrimental, comprising the step of administering to a subject in need thereof an effective amount of an antibody or antigen-binding fragment thereof that specifically binds IL-5, wherein said antibody or antigen-binding fragment comprises:
    (a) a heavy chain amino acid sequence comprising the CDR1, CDR2 and CDR3 amino acid sequences shown in SEQ ID NOS: 8, 10 and 12, respectively; and
    (b) a light chain amino acid sequence comprising the CDR1, CDR2 and CDR3 amino acid sequences shown in SEQ ID NOS: 14, 16 and 18, respectively,
wherein the condition or disorder is asthma.

2. The method according to claim 1, wherein the antibody or antigen-binding fragment decreases or inhibits the infiltration of eosinophils into affected tissue.

3. The method according to claim 2, wherein the anti-IL-5 antibody is administered in conjunction with the administration of another therapeutic agent.

4. A method for treating an IL-5 mediated allergic response in a subject, comprising the step of administering to a subject in need thereof an effective amount of an antibody or antigen-binding fragment thereof that specifically binds IL-5, wherein said antibody or antigen-binding fragment comprises:
    (a) a heavy chain amino acid sequence comprising the CDR1, CDR2 and CDR3 amino acid sequences shown in SEQ ID NOS: 8, 10 and 12, respectively; and
    (b) a light chain amino acid sequence comprising the CDR1, CDR2 and CDR3 amino acid sequences shown in SEQ ID NOS: 14, 16 and 18, respectively.

5. The method of claim 4, wherein the IL-5 mediated allergic response is asthma.

6. A method for treating an IL-5 mediated event selected from the group consisting of:
    (a) eosinophil proliferation, maturation, survival, activation, migration into the bloodstream, adhesion to endothelium, infiltration into tissues;
    (b) pulmonary edema;
    (c) bronchoconstriction;
    (d) airway hyperresponsiveness;
    (e) pulmonary eosinophilia or neutrophilia;
    (f) cutaneous eosinophilia; and
    (g) airway epithelial damage, comprising the step of administering to a subject in need thereof an effective amount of an antibody or antigen-binding fragment thereof that specifically binds IL-5, wherein said antibody or fragment comprises:
    (a) a heavy chain amino acid sequence comprising the CDR1, CDR2 and CDR3 amino acid sequences shown in SEQ ID NOS: 8, 10 and 12, respectively; and
    (b) a light chain amino acid sequence comprising the CDR1, CDR2 and CDR3 amino acid sequences shown in SEQ ID NOS: 14, 16 and 18, respectively.

* * * * *

SEQUENCE LISTING

```
<160> NUMBER OF SEQ ID NOS: 22

<210> SEQ ID NO 1
<211> LENGTH: 2002
<212> TYPE: DNA
<213> ORGANISM: Homo sapiens
<220> FEATURE:
<221> NAME/KEY: V_region
<222> LOCATION: (1)..(414)
<223> OTHER INFORMATION:
<220> FEATURE:
<221> NAME/KEY: CH1 C_region
<222> LOCATION: (415)..(709)
<223> OTHER INFORMATION:
<220> FEATURE:
<221> NAME/KEY: Hinge
<222> LOCATION: (1102)..(1137)
<223> OTHER INFORMATION:
<220> FEATURE:
<221> NAME/KEY: CH2 C_region
<222> LOCATION: (1256)..(1585)
<223> OTHER INFORMATION:
<220> FEATURE:
<221> NAME/KEY: CH3 C_region
<222> LOCATION: (1683)..(2002)
<223> OTHER INFORMATION:

<400> SEQUENCE: 1
atggagtttg ggctgagctg gcttttctt gtggctattt taaaaggtgt ccagtgtgag      60
gtgcagctgt tggagtctgg gggaggcttg gtacagcctg gggggtccct gagactctcc     120
tgtgcagcct ctggattcac ctttagcagc tatgccatga gctgggtccg ccaggctcca     180
gggaaggggc tggagtgggt ctcaactatt agtggtagtg gtggtagcac atactacgca     240
gactccgtga agggccggtt caccatctcc agagacaatt ccaagaacac gctgtatctg     300
caaatgaaca gcctgagagc cgaggacacg gccgtatatt actgtgcgaa agagaggtat     360
aactggaact acctacacta ctggggccag ggaaccctgg tcaccgtctc ctcagctagc     420
accaagggcc catccgtctt ccccctggcg ccctgctcca ggagcacctc cgagagcaca     480
gccgccctgg gctgcctggt caaggactac ttccccgaac cggtgacggt gtcgtggaac     540
tcaggcgccc tgaccagcgg cgtgcacacc ttcccggctg tcctacagtc ctcaggactc     600
tactccctca gcagcgtggt gaccgtgccc tccagcagct gggcacgaa gacctacacc     660
```

```
tgcaacgtag atcacaagcc cagcaacacc aaggtggaca agagagttgg tgagaggcca    720
gcacagggag ggagggtgtc tgctggaagc caggctcagc cctcctgcct ggacgcaccc    780
cggctgtgca gccccagccc agggcagcaa ggcatgcccc atctgtctcc tcacccggag    840
gcctctgacc accccactca tgctcaggga gagggtcttc tggattttc caccaggctc    900 cgggcagcca caggctggat gccctaccc caggccctgc gcatacaggg gcaggtgctg    960
cgctcagacc tgccaagagc catatccggg aggaccctgc cctgaccta agcccacccc   1020 aaaggccaaa ctctccactc cctcagctca gacaccttct ctcctcccag atctgagtaa   1080
ctcccaatct tctctctgca gagtccaaat atggtcccc atgccatca tgcccaggta    1140 agccaaccca ggcctcgccc tccagctcaa ggcgggacag gtgccctaga gtagcctgca   1200
tccagggaca ggccccagcc gggtgctgac gcatccacct ccatctcttc ctcagcacct   1260
gagttcctgg ggggaccatc agtcttcctg ttcccccaa aacccaagga cactctcatg   1320
atctcccgga cccctgaggt cacgtgcgtg gtggtggacg tgagccagga agaccccgag   1380
gtccagttca actggtacgt ggatggcgtg gaggtgcata atgccaagac aaagccgcgg   1440
gaggagcagt tcaacagcac gtaccgtgtg gtcagcgtcc tcaccgtcct gcaccaggac   1500
tggctgaacg gcaaggagta caagtgcaag gtctccaaca aaggcctccc gtcctccatc   1560
gagaaaacca tctccaaagc caaagtggg acccacgggg tgcgagggcc acatggacag   1620
aggtcagctc ggcccaccct ctgccctggg agtgaccgct gtgccaacct ctgtccctac   1680
agggcagccc cgagagccac aggtgtacac cctgccccca tcccaggagg agatgaccaa   1740
gaaccaggtc agcctgacct gcctggtcaa aggcttctac cccagcgaca tcgccgtgga   1800
gtgggagagc aatgggcagc cggagaacaa ctacaagacc acgcctcccg tgctggactc   1860
cgacggctcc ttcttcctct acagcaggct aaccgtggac aagagcaggt ggcaggaggg   1920
gaatgtcttc tcatgctccg tgatgcatga ggctctgcac aaccactaca cacagaagag   1980 cctctcccctg tctctgggta aa                                          2002
```

<210> SEQ ID NO 2
<211> LENGTH: 465
<212> TYPE: PRT
<213> ORGANISM: Homo sapiens
<220> FEATURE:
<221> NAME/KEY: SIGNAL
<222> LOCATION: (1)..(19)
<223> OTHER INFORMATION:
<220> FEATURE:
<221> NAME/KEY: Variable Region
<222> LOCATION: (20)..(138)
<223> OTHER INFORMATION:
<220> FEATURE:
<221> NAME/KEY: CH1 Region
<222> LOCATION: (139)..(236)
<223> OTHER INFORMATION:
<220> FEATURE:
<221> NAME/KEY: Hinge Region
<222> LOCATION: (237)..(248)
<223> OTHER INFORMATION:
<220> FEATURE:
<221> NAME/KEY: CH2 Region
<222> LOCATION: (249)..(358)
<223> OTHER INFORMATION:
<220> FEATURE:
<221> NAME/KEY: CH3 Region
<222> LOCATION: (359)..(465)
<223> OTHER INFORMATION:

<400> SEQUENCE: 2

Met Glu Phe Gly Leu Ser Trp Leu Phe Leu Val Ala Ile Leu Lys Gly

```
1               5                   10                  15
Val Gln Cys Glu Val Gln Leu Leu Glu Ser Gly Gly Gly Leu Val Gln
                20                  25                  30
Pro Gly Gly Ser Leu Arg Leu Ser Cys Ala Ala Ser Gly Phe Thr Phe
                35                  40                  45
Ser Ser Tyr Ala Met Ser Trp Val Arg Gln Ala Pro Gly Lys Gly Leu
                50                  55                  60
Glu Trp Val Ser Thr Ile Ser Gly Ser Gly Gly Ser Thr Tyr Tyr Ala
65                  70                  75                  80
Asp Ser Val Lys Gly Arg Phe Thr Ile Ser Arg Asp Asn Ser Lys Asn
                85                  90                  95
Thr Leu Tyr Leu Gln Met Asn Ser Leu Arg Ala Glu Asp Thr Ala Val
                100                 105                 110
Tyr Tyr Cys Ala Lys Glu Arg Tyr Asn Trp Asn Tyr Leu His Tyr Trp
                115                 120                 125
Gly Gln Gly Thr Leu Val Thr Val Ser Ser Ala Ser Thr Lys Gly Pro
                130                 135                 140
Ser Val Phe Pro Leu Ala Pro Cys Ser Arg Ser Thr Ser Glu Ser Thr
145                 150                 155                 160
Ala Ala Leu Gly Cys Leu Val Lys Asp Tyr Phe Pro Glu Pro Val Thr
                165                 170                 175
Val Ser Trp Asn Ser Gly Ala Leu Thr Ser Gly Val His Thr Phe Pro
                180                 185                 190
Ala Val Leu Gln Ser Ser Gly Leu Tyr Ser Leu Ser Ser Val Val Thr
                195                 200                 205
Val Pro Ser Ser Ser Leu Gly Thr Lys Thr Tyr Thr Cys Asn Val Asp
                210                 215                 220
His Lys Pro Ser Asn Thr Lys Val Asp Lys Arg Val Glu Ser Lys Tyr
225                 230                 235                 240
Gly Pro Pro Cys Pro Ser Cys Pro Ala Pro Glu Phe Leu Gly Gly Pro
                245                 250                 255
Ser Val Phe Leu Phe Pro Pro Lys Pro Lys Asp Thr Leu Met Ile Ser
                260                 265                 270
Arg Thr Pro Glu Val Thr Cys Val Val Val Asp Val Ser Gln Glu Asp
                275                 280                 285
Pro Glu Val Gln Phe Asn Trp Tyr Val Asp Gly Val Glu Val His Asn
                290                 295                 300
Ala Lys Thr Lys Pro Arg Glu Glu Gln Phe Asn Ser Thr Tyr Arg Val
305                 310                 315                 320
Val Ser Val Leu Thr Val Leu His Gln Asp Trp Leu Asn Gly Lys Glu
                325                 330                 335
Tyr Lys Cys Lys Val Ser Asn Lys Gly Leu Pro Ser Ser Ile Glu Lys
                340                 345                 350
Thr Ile Ser Lys Ala Lys Gly Gln Pro Arg Glu Pro Gln Val Tyr Thr
                355                 360                 365
Leu Pro Pro Ser Gln Glu Glu Met Thr Lys Asn Gln Val Ser Leu Thr
                370                 375                 380
Cys Leu Val Lys Gly Phe Tyr Pro Ser Asp Ile Ala Val Glu Trp Glu
385                 390                 395                 400
Ser Asn Gly Gln Pro Glu Asn Asn Tyr Lys Thr Thr Pro Pro Val Leu
                405                 410                 415
Asp Ser Asp Gly Ser Phe Phe Leu Tyr Ser Arg Leu Thr Val Asp Lys
                420                 425                 430
```

Ser Arg Trp Gln Glu Gly Asn Val Phe Ser Cys Ser Val Met His Glu
         435                 440                 445

Ala Leu His Asn His Tyr Thr Gln Lys Ser Leu Ser Leu Ser Leu Gly
     450                 455                 460

Lys
465

<210> SEQ ID NO 3
<211> LENGTH: 708
<212> TYPE: DNA
<213> ORGANISM: Homo sapiens

<400> SEQUENCE: 3
atggacatga gggtccctgc tcagctcctg gggctcctgc tgctctggct ctcaggtgcc      60
agatgtgaca tccagatgac ccagtctcca tcctccctgt ctgcatctgt gggagacaga     120
gtcaccatca cttgccaggc gagtcaggac attatcaact atttaaattg gtatcagcag     180
aaaccaggga agcccctaa actcctgatc tacagtgctt ccaatttgga aacaagagtc      240
ccatcaaggt tcagtggaag tggttctggg acagatttta ctttcaccat cagcagcctg     300
cagcctgaag atattgcaac atattattgt caacagtatg ataatcaccc gctcactttc     360
ggcggaggga ccaaggtgga gatcagacga actgtggctg caccatctgt cttcatcttc     420
ccgccatctg atgagcagtt gaaatctgga actgcctctg ttgtgtgcct gctgaataac     480
ttctatccca gagaggccaa agtacagtgg aaggtggata acgccctcca atcgggtaac     540
tcccaggaga gtgtcacaga gcaggacagc aaggacagca cctacagcct cagcagcacc     600
ctgacgctga gcaaagcaga ctacgagaaa cacaaagtct acgcctgcga agtcacccat     660
cagggcctga gctcgcccgt cacaaagagc ttcaacaggg gagagtgt               708

<210> SEQ ID NO 4
<211> LENGTH: 236
<212> TYPE: PRT
<213> ORGANISM: Homo sapiens
<220> FEATURE:
<221> NAME/KEY: Signal Peptide
<222> LOCATION: (1)..(22)
<223> OTHER INFORMATION:

<400> SEQUENCE: 4

Met Asp Met Arg Val Pro Ala Gln Leu Leu Gly Leu Leu Leu Leu Trp
1               5                   10                  15

Leu Ser Gly Ala Arg Cys Asp Ile Gln Met Thr Gln Ser Pro Ser Ser
             20                  25                  30

Leu Ser Ala Ser Val Gly Asp Arg Val Thr Ile Thr Cys Gln Ala Ser
         35                  40                  45

Gln Asp Ile Ile Asn Tyr Leu Asn Trp Tyr Gln Gln Lys Pro Gly Lys
     50                  55                  60

Ala Pro Lys Leu Leu Ile Tyr Ser Ala Ser Asn Leu Glu Thr Arg Val
65                  70                  75                  80

Pro Ser Arg Phe Ser Gly Ser Gly Ser Gly Thr Asp Phe Thr Phe Thr
                 85                  90                  95

Ile Ser Ser Leu Gln Pro Glu Asp Ile Ala Thr Tyr Tyr Cys Gln Gln
            100                 105                 110

Tyr Asp Asn His Pro Leu Thr Phe Gly Gly Gly Thr Lys Val Glu Ile
         115                 120                 125

Arg Arg Thr Val Ala Ala Pro Ser Val Phe Ile Phe Pro Pro Ser Asp

-continued

```
                    130                 135                 140
Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 5
<211> LENGTH: 414
<212> TYPE: DNA
<213> ORGANISM: Homo sapiens

<400> SEQUENCE: 5
atggagtttg ggctgagctg gcttttcctt gtggctattt taaaaggtgt ccagtgtgag      60
gtgcagctgt tggagtctgg gggaggcttg gtacagcctg ggggtccct  gagactctcc     120 tgtgcagcct ctggattcac ctttagcagc tatgccatga gctgggtccg ccaggctcca     180 gggaagggc tggagtgggt ctcaactatt agtggtagtg gtggtagcac atactacgca      240
gactccgtga agggccggtt caccatctcc agagacaatt ccaagaacac gctgtatctg     300
caaatgaaca gcctgagagc cgaggacacg gccgtatatt actgtgcgaa agagaggtat     360
aactggaact acctacacta ctggggccag ggaaccctgg tcaccgtctc ctca           414

<210> SEQ ID NO 6
<211> LENGTH: 119
<212> TYPE: PRT
<213> ORGANISM: Homo sapiens

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Arg Tyr Asn Trp Asn Tyr Leu His Tyr Trp Gly Gln Gly
            100                 105                 110

Thr Leu Val Thr Val Ser Ser
        115

<210> SEQ ID NO 7
<211> LENGTH: 15
<212> TYPE: DNA
<213> ORGANISM: Homo sapiens
```

```
<400> SEQUENCE: 7
agctatgcca tgagc                                                     15

<210> SEQ ID NO 8
<211> LENGTH: 5
<212> TYPE: PRT
<213> ORGANISM: Homo sapiens

<400> SEQUENCE: 8

Ser Tyr Ala Met Ser
1               5

<210> SEQ ID NO 9
<211> LENGTH: 51
<212> TYPE: DNA
<213> ORGANISM: Homo sapiens

<400> SEQUENCE: 9
actattagtg gtagtggtgg tagcacatac tacgcagact ccgtgaaggg c              51

<210> SEQ ID NO 10
<211> LENGTH: 17
<212> TYPE: PRT
<213> ORGANISM: Homo sapiens

<400> SEQUENCE: 10

Thr Ile Ser Gly Ser Gly Gly Ser Thr Tyr Tyr Ala Asp Ser Val Lys
1               5                   10                  15
Gly

<210> SEQ ID NO 11
<211> LENGTH: 30
<212> TYPE: DNA
<213> ORGANISM: Homo sapiens

<400> SEQUENCE: 11
gagaggtata actggaacta cctacactac                                     30

<210> SEQ ID NO 12
<211> LENGTH: 10
<212> TYPE: PRT
<213> ORGANISM: Homo sapiens

<400> SEQUENCE: 12

Glu Arg Tyr Asn Trp Asn Tyr Leu His Tyr
1               5                   10

<210> SEQ ID NO 13
<211> LENGTH: 33
<212> TYPE: DNA
<213> ORGANISM: Homo sapiens

<400> SEQUENCE: 13
caggcgagtc aggacattat caactattta aat                                 33

<210> SEQ ID NO 14
<211> LENGTH: 11
<212> TYPE: PRT
<213> ORGANISM: Homo sapiens

<400> SEQUENCE: 14

Gln Ala Ser Gln Asp Ile Ile Asn Tyr Leu Asn
```

<210> SEQ ID NO 15
<211> LENGTH: 20
<212> TYPE: DNA
<213> ORGANISM: Homo sapiens

<400> SEQUENCE: 15
gtgcttccaa tttggaaaca                                              20

<210> SEQ ID NO 16
<211> LENGTH: 7
<212> TYPE: PRT
<213> ORGANISM: Homo sapiens

<400> SEQUENCE: 16

Ser Ala Ser Asn Leu Glu Thr
1               5

<210> SEQ ID NO 17
<211> LENGTH: 27
<212> TYPE: DNA
<213> ORGANISM: Homo sapiens

<400> SEQUENCE: 17
caacagtatg ataatcaccc gctcact                                      27

<210> SEQ ID NO 18
<211> LENGTH: 9
<212> TYPE: PRT
<213> ORGANISM: Homo sapiens

<400> SEQUENCE: 18

Gln Gln Tyr Asp Asn His Pro Leu Thr
1               5

<210> SEQ ID NO 19
<211> LENGTH: 31
<212> TYPE: DNA
<213> ORGANISM: Homo sapiens

<400> SEQUENCE: 19
ggaagaattc accctgtgca ggagtcagtc c                                 31

<210> SEQ ID NO 20
<211> LENGTH: 36
<212> TYPE: DNA
<213> ORGANISM: Homo sapiens

<400> SEQUENCE: 20
tgagatcgag ggcccttct ccctctaaca ctctcc                             36

<210> SEQ ID NO 21
<211> LENGTH: 34
<212> TYPE: DNA
<213> ORGANISM: Homo sapiens

<400> SEQUENCE: 21
ccggaattcc agagagaact caccatggag tttg                              34

<210> SEQ ID NO 22
<211> LENGTH: 40

```
<212> TYPE: DNA
<213> ORGANISM: Homo sapiens

<400> SEQUENCE: 22
gagagagagc tagctgagga gacggtgacc agggttccct                              40
```